(12) United States Patent
Vrijbloed et al.

(10) Patent No.: US 7,855,179 B2
(45) Date of Patent: Dec. 21, 2010

(54) TEMPLATE-FIXED PEPTIDOMIMETICS WITH ANTIMICROBIAL ACTIVITY

(75) Inventors: Jan Wim Vrijbloed, Möhlin (CH); Daniel Obrecht, Bättwil (CH); John Anthony Robinson, Wermatswil (CH); Sergio Locurio, Reinach (CH); Frank Gombert, Huttingen (DE); Christian Ludin, Oberwil (CH); Alexander Lederer, Basel (CH); Shivaprasad Shankaramma, Rockville, MD (US)

(73) Assignees: Polyphor Ltd., Allschwil (CH); Universität Zürich, Zürich (CH)

( * ) Notice: Subject to any disclaimer, the term of this patent is extended or adjusted under 35 U.S.C. 154(b) by 1158 days.

(21) Appl. No.: 10/530,335

(22) PCT Filed: Oct. 2, 2002

(86) PCT No.: PCT/EP02/11048
§ 371 (c)(1),
(2), (4) Date: Jun. 13, 2006

(87) PCT Pub. No.: WO2004/033489
PCT Pub. Date: Apr. 22, 2004

(65) Prior Publication Data
US 2007/0054840 A1    Mar. 8, 2007

(51) Int. Cl.
*A61K 38/10* (2006.01)
*C07K 7/08* (2006.01)
*C07K 1/36* (2006.01)

(52) U.S. Cl. .......................... 514/14; 530/327; 530/333

(58) Field of Classification Search .................. None
See application file for complete search history.

(56) References Cited

FOREIGN PATENT DOCUMENTS

| WO | WO 01/16161 | 3/2001 |
|----|-------------|--------|
| WO | WO 02/70547 | 9/2002 |

OTHER PUBLICATIONS

Zuckermann et al (Polymer Preprints 35(2) 1994 pp. 975-976).*
Miller et al (Bioorganic and Medicinal Chemistry Letters v4 1994 pp. 2657-2662).*
Goodson et al (Antimicrobial agents and chemotherapy v43 1999, pp. 1429-1434).*
J. Rudinger. In: Peptide Hormones, JA Parsons, Ed. (1976) 1-7.*
* cited by examiner

*Primary Examiner*—Andrew D Kosar
(74) *Attorney, Agent, or Firm*—Hoffmann & Baron, LLP

(57) ABSTRACT

Template-fixed β-hairpin peptidomimetics of the general formula (I), wherein Z is a template-fixed chain of 12 α-amino acid residues which, depending on their positions in the chain (counted starting from the N-terminal amino acid) are Gly or Pro, or of certain types, at least one of these residues being of the type of N-substituted glycines, which types, as the remaining symbols in the above formula, are defined in the description and the claims, and salts thereof, have the property to inhibit the growth of or to kill microorganisms. They can be used as disinfectants for foodstuffs, cosmetics, medicaments or other nutrient-containing materials or as medicaments to treat or prevent infections. These β-hairpin peptidomimetics can be manufactured by processes which are based on a mixed solid- and solution phase synthetic strategy.

(I)

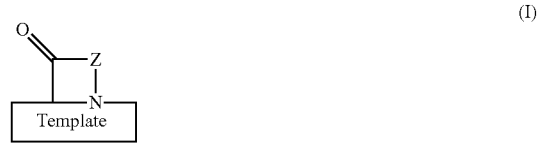

25 Claims, No Drawings

TEMPLATE-FIXED PEPTIDOMIMETICS WITH ANTIMICROBIAL ACTIVITY

CROSS-REFERENCE TO RELATED APPLICATIONS

This application is a U.S. National Phase Application of PCT/EP2002/011048, filed Oct. 2, 2002, the entire contents of which are incorporated herein by reference.

The present invention provides template-fixed β-hairpin peptidomimetics incorporating a template-fixed chain of 12 α-amino acid residues which, depending on their positions in the chain, are Gly or Pro, or of certain types, as defined herein below, at least one of these residues being of the type of N-substituted glycines These template-fixed β-hairpin mimetics have broad spectrum antimicrobial activity. In addition, the present invention provides efficient synthetic processes by which these compounds can, if desired, be made in parallel library-format. These β-hairpin peptidomimetics show improved efficacy, bioavailability, half-life and most importantly a significantly enhanced ratio between antibacterial on the one hand, and hemolysis of red blood cells on the other.

The growing problem of microbial resistance to established antibiotics has stimulated intense interest in developing novel antimicrobial agents with new modes of action (H. Breithaupt, Nat. Biotechnol. 1999, 17, 1165-1169). One emerging class of antibiotics is based on naturally occurring cationic peptides (T. Ganz, R. I. Lehrer, Mol. Medicine Today 1999, 5, 292-297; R. M. Epand, H. J. Vogel, Biochim. Biophys. Acta 1999, 1462, 11-28). These include disulfide-bridged β-hairpin and β-sheet peptides (such as the protegrins [V. N. M.; O. V. Shamova, H. A. Korneva, R. I. Lehrer, FEBS Lett. 1993, 327, 231-236], tachyplesins [T. Nakamura, H. Furunaka, T. Miyata, F. Tokunaga, T. Muta, S. Iwanaga, M. Niwa, T. Takao, Y. Shimonishi, Y. J. Biol. Chem. 1988, 263, 16709-16713], and the defensins [R. I. Lehrer, A. K. Lichtenstein, T. Ganz, Annu. Rev. Immunol. 1993, 11, 105-128], amphipathic α-helical peptides (e.g. cecropins, dermaseptins, magainins, and mellitins [A. Tossi, L. Sandri, A. Giangaspero, Biopolymers 2000, 55, 4-30]), as well as other linear and loop-structured peptides. Although the mechanisms of action of antimicrobial cationic peptides are not yet fully understood, their primary site of interaction is the microbial cell membrane (H. W. Huang, Biochemistry 2000, 39, 8347-8352). Upon exposure to these agents, the cell membrane undergoes permeabilization, which is followed by rapid cell death. However, more complex mechanisms of action, for example, involving receptor-mediated signaling, cannot presently be ruled out (M. Wu, E. Maier, R. Benz, R. E. Hancock, Biochemistry 1999, 38, 7235-7242).

The antimicrobial activities of many of these cationic peptides usually correlate with their preferred secondary structures, observed either in aqueous solution or in membrane-like environments (N. Sitaram, R. Nagaraj, Biochim. Biophys. Acta 1999, 1462, 29-54). Structural studies by nuclear magnetic resonance (NMR) spectroscopy have shown that cationic peptides such as protegrin 1 (A. Aumelas, M. Mangoni, C. Roumestand, L. Chiche, E. Despaux, G. Grassy, B. Calas, A. Chavanieu, A. Eur. J. Biochem. 1996, 237, 575-583; R. L. Fahrner, T. Dieckmann, S. S. L. Harwig, R. I. Lehrer, D. Eisenberg, J. Feigon, J. Chem. Biol. 1996, 3, 543-550) and tachyplesin I (K. Kawano, T. Yoneya, T. Miyata, K. Yoshikawa, F. Tokunaga, Y. Terada, S. J. Iwanaga, S. J. Biol. Chem. 1990, 265, 15365-15367) adopt well defined β-hairpin conformations, due to the constraining effect of two disulfide bridges. In protegrin analogues lacking one or both of these disulfide bonds, the stability of the β-hairpin conformation is diminished, and the antimicrobial activity is reduced (J. Chen, T. J. Falla, H. J. Liu, M. A. Hurst, C. A. Fujii, D. A. Mosca, J. R. EmbreeD. J. Loury, P. A. Radel, C. C. Chang, L. Gu, J. C. Fiddes, Biopolymers 2000, 55, 88-98; S. L. Harwig, A. Waring, H. J. Yang, Y. Cho, L. Tan, R. I. Lehrer, R. J. Eur. J. Biochem. 1996, 240, 352-357; M. E. Mangoni, A. Aumelas, P. Charnet, C. Roumestand, L. Chiche, E. Despaux, G. Grassy, B. Calas, A. Chavanieu, FEBS Lett. 1996, 383, 93-98; H. Tamamura, T. Murakami, S. Noriuchi, K. Sugihara, A. Otaka, W. Takada, T. Ibuka, M. Waki, N. Tamamoto, N. Fujii, Chem. Pharm. Bull. 1995, 43, 853-858). Similar observations have been made in analogues of tachyplesin I (H. Tamamura, R. Ikoma, M. Niwa, S. Funakoshi, T. Murakami, N. Fujii, Chem. Pharm. Bull. 1993, 41, 978-980) and in hairpin-loop mimetics of rabbit defensin NP-2 (S. Thennarasu, R. Nagaraj, Biochem. Biophys. Res. Comm. 1999, 254, 281-283). These results show that the β-hairpin structure plays an important role in the antimicrobial activity and stability of these protegrin-like peptides. In the case of the cationic peptides preferring α-helical structures, the amphililic structure of the helix appears to play a key role in determining antimicrobial activity (A. Tossi, L. Sandri, A. Giangaspero, A. Biopolymers 2000, 55, 4-30). Gramicidin S is a backbone-cyclic peptide with a well defined β-hairpin structure (S. E. Hull, R. Karlsson, P. Main, M. M. Woolfson, E. J. Dodson, Nature 1978, 275, 206-275) that displays potent antimicrobial activity against gram-positive and gram-negative bacteria (L. H. Kondejewski, S. W. Farmer, D. S. Wishart, R. E. Hancock, R. S. Hodges, Int. J. Peptide Prot. Res. 1996, 47, 460-466). The high hemolytic activity of gramicidin S has, however, hindered its widespread use as an antibiotic. Recent structural studies by NMR have indicated that the high hemolytic activity apparently correlates with the highly amphipathic nature of this cyclic β-hairpin-like molecule, but that it is possible to dissociate antimicrobial and hemolytic activities by modulating the conformation and amphiphilicity (L. H. Kondejewski, M. Jelokhani-Niaraki, S. W. Farmer, B. Lix, M. Kay, B. D. Sykes, R. E. Hancock, R. S. Hodges, J. Biol. Chem. 1999, 274, 13181-13192; C. McInnesL. H. Kondejewski, R. S. Hodges, B. D. Sykes, J. Biol. Chem. 2000, 275, 14287-14294).

A new cyclic antimicrobial peptide RTD-1 was reported recently from primate leukocytes (Y.-Q. Tang, J. Yuan, G. Ösapay, K. Ösapay, D. Tran, C. J. Miller, A. J. Oellette, M. E. Selsted, Science 1999, 286, 498-502. This peptide contains three disulfide bridges, which act to constrain the cyclic peptide backbone into a hairpin geometry. Cleavage of the three disulfide bonds leads to a significant loss of antimicrobial activity. Analogues of protegrins (S. P. Tam, C. Wu, J.-L. Yang, Eur. J. Biochem. 2000, 267, 3289-3300) and tachyplesins (J.-P. Tam, Y.-A. Lu, J.-L. Yang, Biochemistry 2000, 39, 7159-7169; N. Sitaram, R. Nagaraij, Biochem. Biophys. Res. Comm. 2000, 267, 783-790) containing a cyclic peptide backbone, as well as multiple disulfide bridges to enforce a amphiphilic hairpin structure, have also been reported. In these cases, removal of all the cystine constraints does not always lead to a large loss of antimicrobial activity, but does modulate the membranolytic selectivity (J. P. Tam, C. Wu, J.-L. Yang, Eur. J. Biochem. 2000, 267, 3289-3300).

A key issue in the design of new cationic antimicrobial peptides is selectivity. The naturally occurring protegrins and tachyplesins exert a significant hemolytic activity against human red blood cells. This is also the case for protegrin analogues such as IB367 (J. Chen, T. J. Falla, H. J. Liu, M. A. Hurst, C. A. Fujii, D. A. Mosca, J. R. Embree, D. J. Loury, P. A. Radel, C. C. Chang, L. Gu, J. C. Fiddes, Biopolymers 2000, 55, 88-98; C. Chang, L. Gu, J. Chen, U.S. Pat. No. 5,916,872, 1999). This high hemolytic activity essentially obviates its use in vivo, and represents a serious disadvantage in clinical applications. Also, the antibiotic activity of analogues often decreases significantly with increasing salt concentration, such that under in vivo conditions (ca. 100-150 mM NaCl) the antimicrobial activity may be severely reduced. Before intravenous use can be considered, the general toxicity, protein-binding activity in blood serum, as well as protease stability become serious issues which must be adequately addressed.

Protegrin 1 exhibits potent and similar activity against gram-positive and gram-negative bacteria as well as fungi in both low- and high-salt assays. This broad antimicrobial activity combined with a rapid mode of action, and their ability to kill bacteria resistant to other classes of antibiotics, make them attractive targets for development of clinically useful antibiotics. The activity against gram-positive bacteria is typically higher than against gram-negative bacteria. However, protegrin 1 also exhibits a high hemolytic activity against human red blood cells, and hence a low selectivity towards microbial cells. Oriented CD experiments (W. T. Heller, A. J. Waring, R. I. Lehrer, H. W. Huang, *Biochemistry* 1998, 37, 17331-17338) indicate that protegrin 1 may exist in two different states as it interacts with membranes, and these states are strongly influenced by lipid composition. Studies of cyclic protegrin analogues (J.-P. Tam, C. Wu, J.-L. Yang, *Eur. J. Biochem.* 2000, 267, 3289-3300) have revealed, that an increase in the conformational rigidity, resulting from backbone cyclization and multiple disulfide bridges, may confer membranolytic selectivity that dissociates antimicrobial activity from hemolytic activity, at least in the series of compounds studied.

Protegrin 1 is an 18 residues linear peptide, with an amidated carboxyl terminus and two disulfide bridges. Tachyplesin I contains 17 residues, also has an amidated carboxyl terminus and contains two disulfide bridges. Recently described backbone-cyclic protegrin and tachyplesin analogues typically contain 18 residues and up to three disulfide bridges (J. P. Tam, C. Wu, J.-L. Yang, *Eur. J. Biochem.* 2000, 267, 3289-3300; J. P. Tam, Y.-A. Lu, J.-L. Yang, *Biochemistry* 2000, 39, 7159-7169; N. Sitaram, R. Nagaraij, *Biochem. Biophys. Res. Comm.* 2000, 267, 783-790).

Cathelicidin, a 37-residue linear helical-type cationic peptide, and analogues are currently under investigation as inhaled therapeutic agents for cystic fibrosis (CF) lung disease (L. Saiman, S. Tabibi, T. D. Starner, P. San Gabriel, P. L. Winokur, H. P. Jia, P. B. McGray, Jr., B. F. Tack, *Antimicrob. Agents and Chemother.* 2001, 45, 2838-2844; R. E. W. Hancock R. Lehrer, *Trends Biotechnol.* 1998, 16, 82-88). Over 80% of CF patients become chronically infected with *pseudomonas aeruginosa* (C. A. Demko, P. J. Biard, P. B. Davies, *J. Clin. Epidemiol.* 1995, 48, 1041-1049; E. M. Kerem, R. Gold, H. Levinson, *J. Pediatr.* 1990, 116, 714-719).

In the compounds described below, a new strategy is introduced to stabilize β-hairpin conformations in backbone-cyclic cationic peptide mimetic exhibiting antimicrobial activity. This involves transplanting the cationic and hydrophobic hairpin sequence onto a template, whose function is to restrain the peptide loop backbone into a hairpin geometry. The rigidity of the hairpin may be further influenced by introducing a disulfide bridge. Template-bound hairpin mimetic peptides have been described in the literature (D, Obrecht, M. Altorfer, J. A. Robinson, *Adv. Med. Chem.* 1999, 4, 1-68; J. A. Robinson, *Syn. Lett.* 2000, 4, 429-441), but such molecules have not previously been evaluated for development of antimicrobial peptides. However, the ability to generate β-hairpin peptidomimetics using combinatorial and parallel synthesis methods has now been established (L. Jiang, K. Moehle, B. Dhanapal, D. Obrecht, J. A. Robinson, *Helv. Chim. Acta.* 2000, 83, 3097-3112). In addition incorporation of designated peptoid structure elements into template-bound hairpin mimetics have not previously been evaluated for development of antimicrobial peptides.

These methods allow the synthesis and screening of large hairpin mimetic libraries, which in turn considerably facilitates structure-activity studies, and hence the discovery of new molecules with potent antimicrobial and low hemolytic activity to human red blood cells. Furthermore, the present strategy allows to synthesize β-hairpin peptidomimetics with novel selectivities towards different types of pathogens, e.g. towards various multi-drug resistant *pseudomonas* strains. β-Hairpin peptidomimetics obtained by the approach described here can be used amongst other applications, e.g. as broad spectrum antibiotics.

The β-hairpin peptidomimetics of the present invention are compounds of the general formula

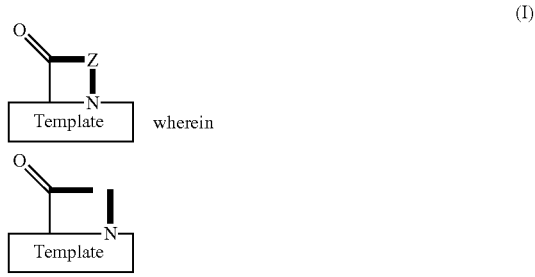

wherein is a group of one of the formulae

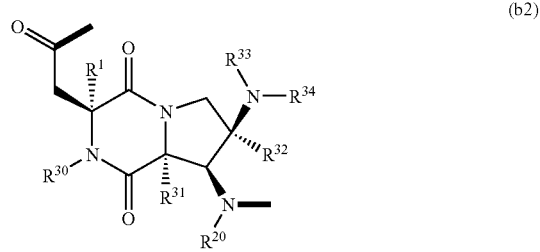

-continued
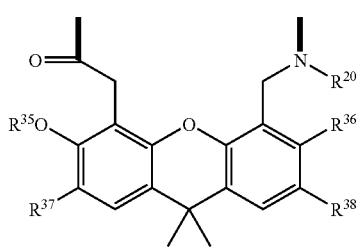
(c1)
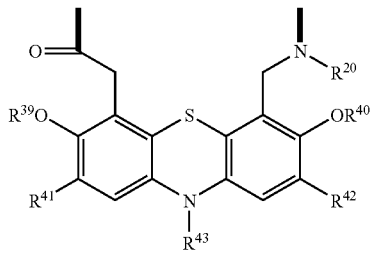
(c2)
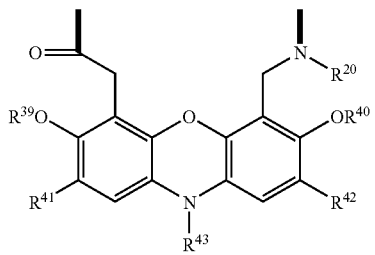
(c3)
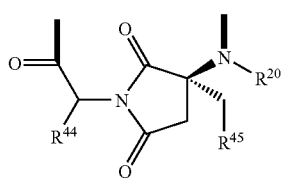
(d)
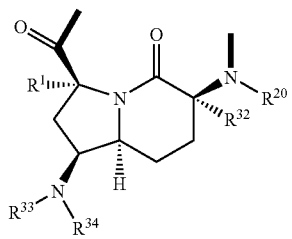
(e1)
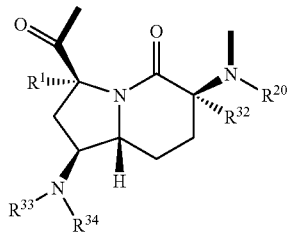
(e2)
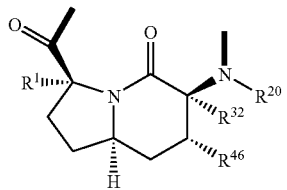
(e3)
-continued
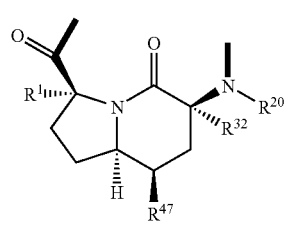
(e4)
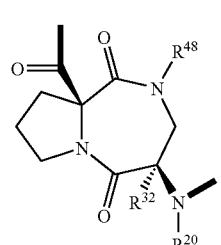
(f)
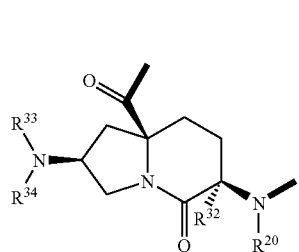
(g)
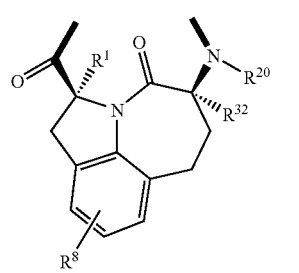
(h)
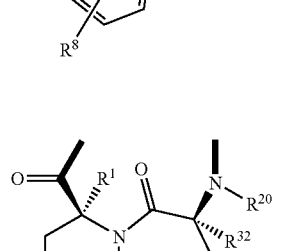
(i1)
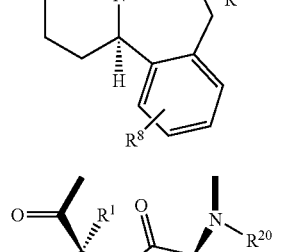
(i2)
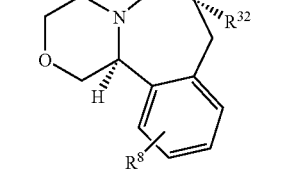

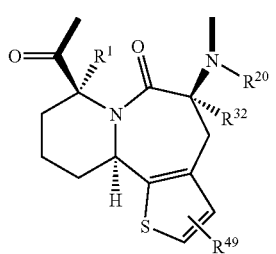 (i3)
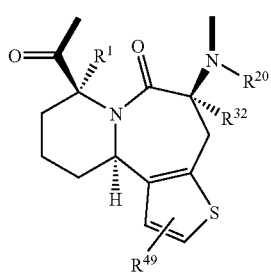 (i4)
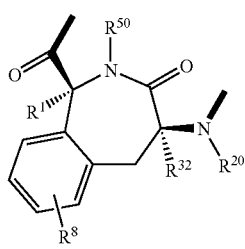 (j)
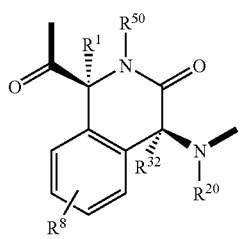 (k)
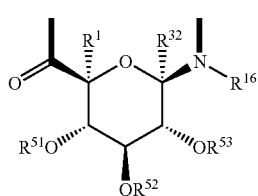 (l)
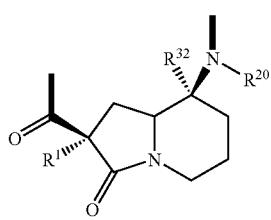 (m)
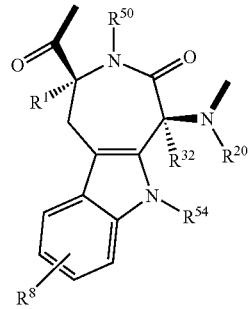 (n)
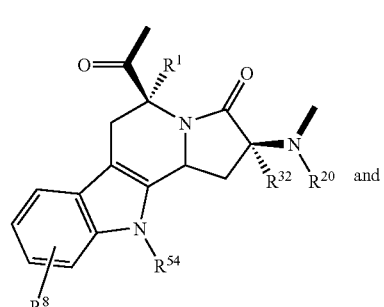 (o)
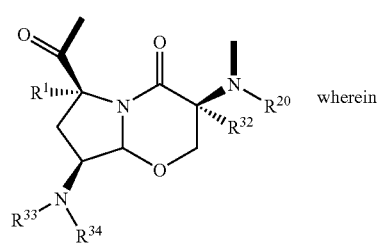 (p) wherein
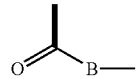
is the residue of an L-α-amino acid with B being a residue of formula —NR$^{20}$CH(R$^{71}$)— or the enantiomer of one of the groups A1 to A69 as defined hereinafter,
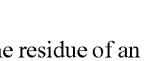
is a group of one of the formulae
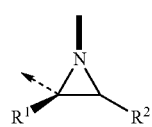 A1
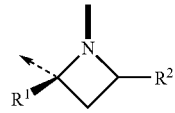 A2

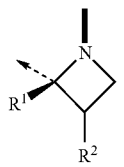 A3
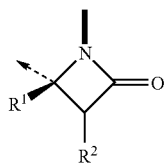 A4
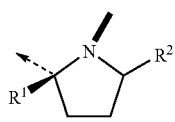 A5
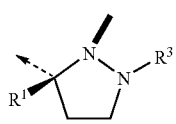 A6
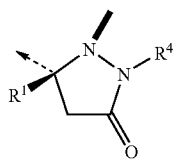 A7
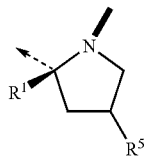 A8
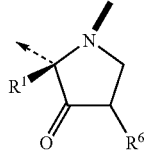 A9
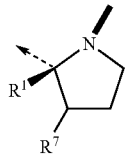 A10
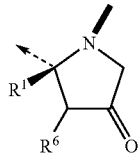 A11
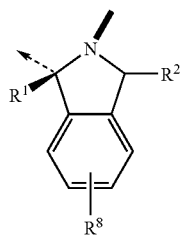 A12
A13
A14
A15
A16
A17
A18
A19

-continued
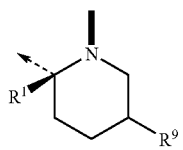 A20
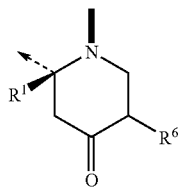 A21
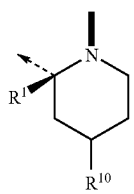 A22
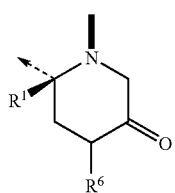 A23
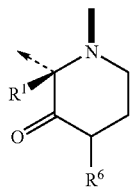 A24
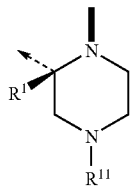 A25
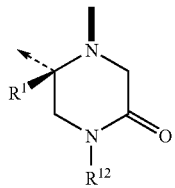 A26
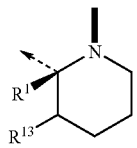 A27
-continued
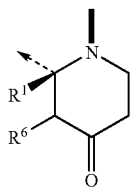 A28
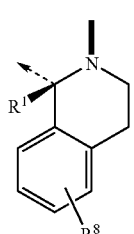 A29
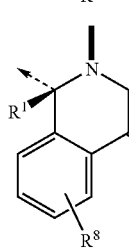 A30
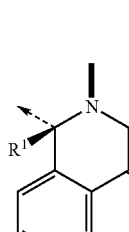 A31
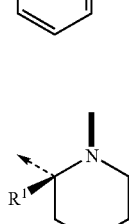 A32
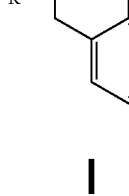 A33
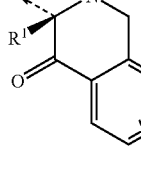 A34
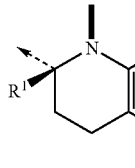

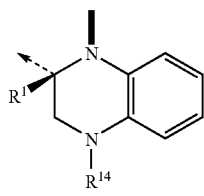 A35
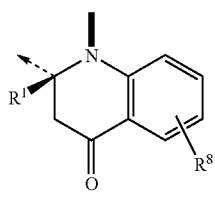 A36
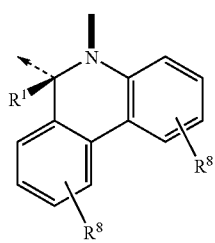 A37
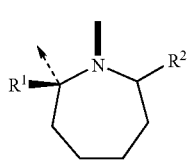 A38
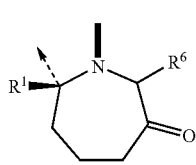 A39
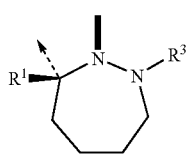 A40
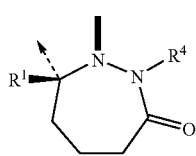 A41
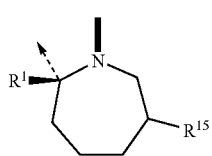 A42
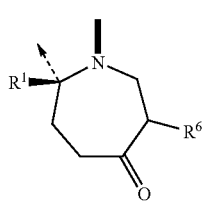 A43
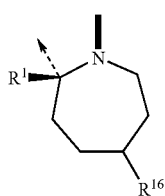 A44
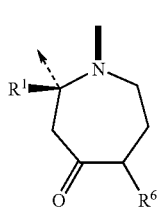 A45
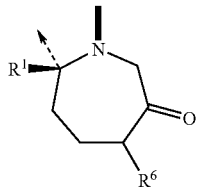 A46
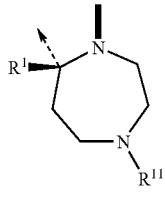 A47
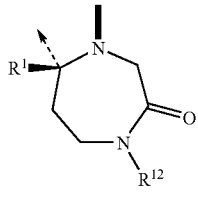 A48
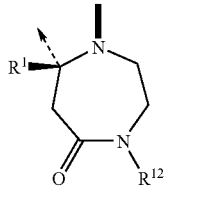 A49
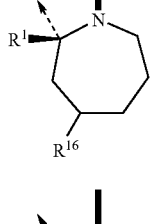 A50
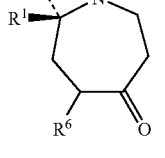 A51
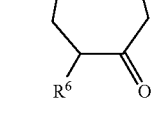

-continued
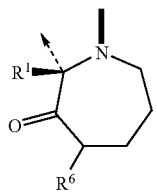 A52
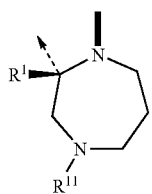 A53
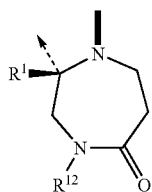 A54
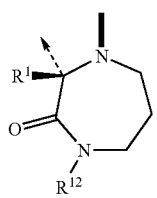 A55
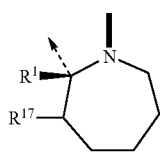 A56
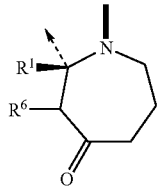 A57
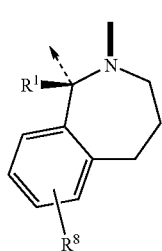 A58
-continued
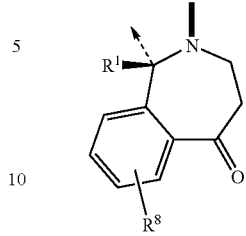 A59
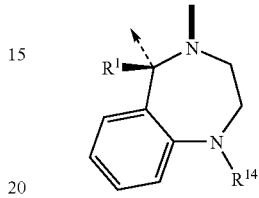 A60
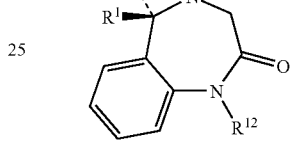 A61
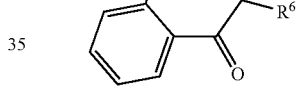 A62
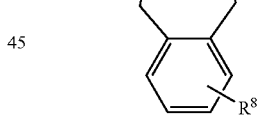 A63
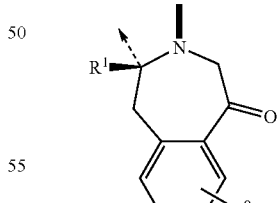 A64
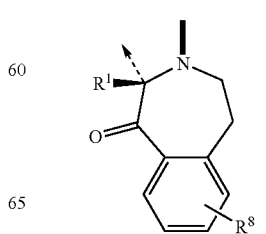 A65

-continued
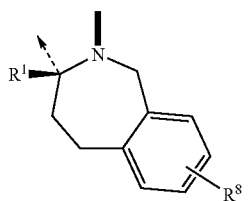 A66
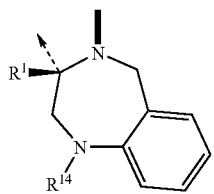 A67
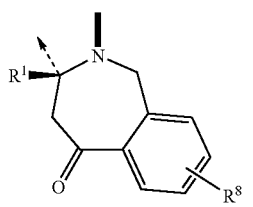 A68
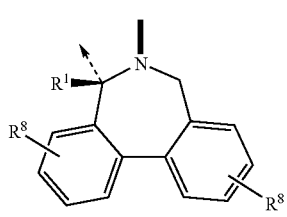 A69
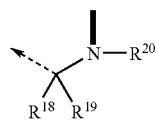 A70
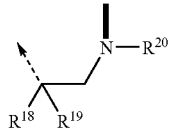 A71
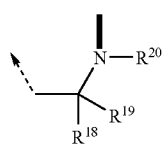 A72
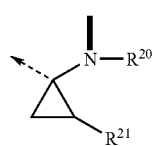 A73
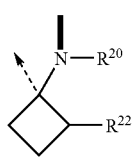 A74
-continued
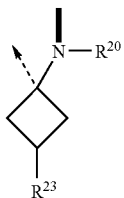 A75
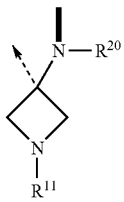 A76
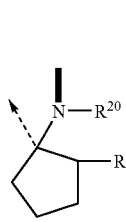 A77
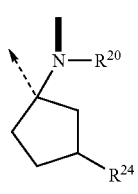 A78
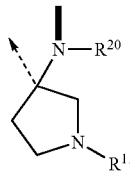 A79
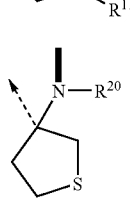 A80
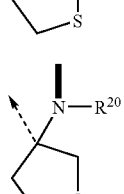 A81
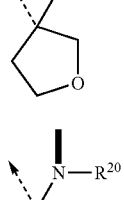 A82
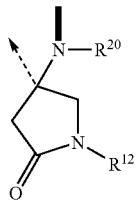

-continued
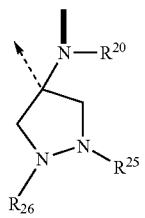 A83
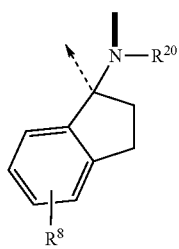 A84
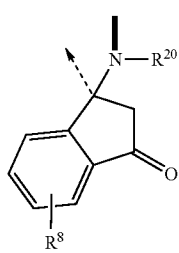 A85
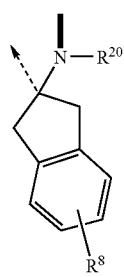 A86
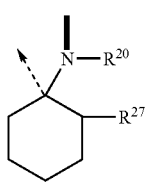 A87
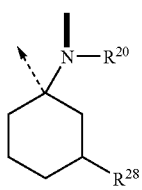 A88
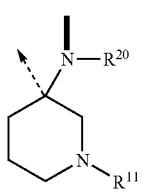 A89
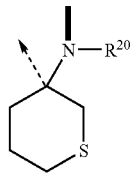 A90
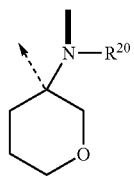 A91
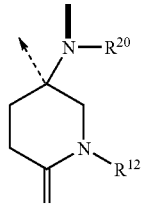 A92
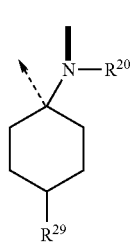 A93
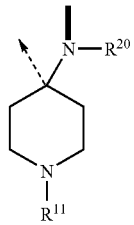 A94
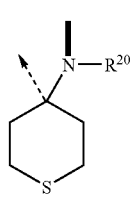 A95
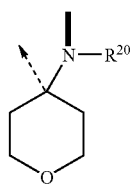 A96

-continued

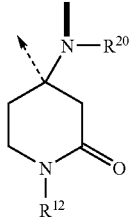
A97

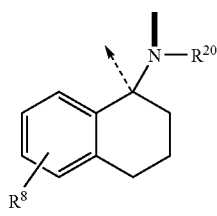
A98

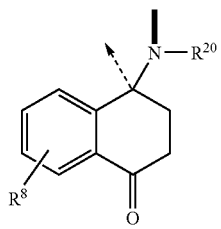
A99

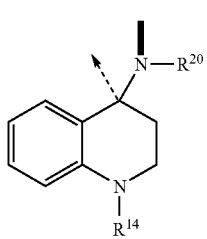
A100

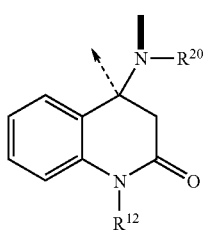
A101

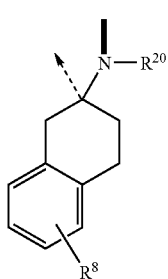
A102

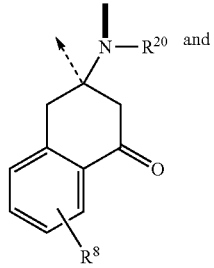
A103

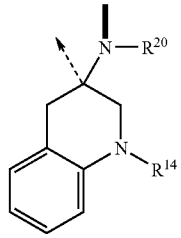
A104 and $R^1$ is H; lower alkyl; or aryl-lower alkyl;

$R^2$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})_2COOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^3$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^4$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_p(CHR^{61})_sCOOR^{57}$; —$(CH_2)_p(CHR^{61})_sCONR^{58}R^{59}$; —$(CH_2)_p(CHR^{61})_sPO(OR^{60})_2$; —$(CH_2)_p(CHR^{61})_sSO_2R^{62}$; or —$(CH_2)_o(CHR^{61})_sC_6H_4R^8$;

$R^5$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^6$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^7$ is alkyl; alkenyl; —$(CH_2)_q(CHR^{61})_sOR^{55}$; —$(CH_2)_q(CHR^{61})_sNR^{33}R^{34}$; —$(CH_2)_q(CHR^{61})_sOCONR^{33}R^{75}$; —$(CH_2)_q(CHR^{61})_sNR^{30}CONR^{33}R^{82}$; —$(CH_2)_r(CHR^{61})_sCOOR^{57}$; —$(CH_2)_r(CHR^{61})_sCONR^{58}R^{59}$; —$(CH_2)_r(CHR^{61})_sPO(OR^{60})_2$; —$(CH_2)_r(CHR^{61})_sSO_2R^{62}$; or —$(CH_2)_r(CHR^{61})_sC_6H_4R^8$;

$R^8$ is H; Cl; F; CF$_3$; NO$_2$; lower alkyl; lower alkenyl; aryl; aryl-lower alkyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$COR$^{64}$;

$R^9$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

$R^{10}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

$R^{11}$ is H; alkyl; alkenyl; —(CH$_2$)$_m$(CHR$^{61}$)$_s$OR$^{55}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

$R^{12}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_r$(CHR$^{61}$)$_s$COOR$^{57}$; —(CH$_2$)$_r$(CHR$^{61}$)$_s$CONR$^{58}$R$^{59}$; —(CH$_2$)$_r$(CHR$^{61}$)$_s$PO(OR$^{60}$)$_2$; —(CH$_2$)$_r$(CHR$^{61}$)$_s$SO$_2$R$^{62}$; or —(CH$_2$)$_r$(CHR$^{61}$)$_s$C$_6$H$_4$R$^8$;

$R^{13}$ is alkyl; alkenyl; —(CH$_2$)$_q$(CHR$^{61}$)$_s$OR$^{55}$; —(CH$_2$)$_q$(CHR$^{61}$)$_s$SR$^{56}$; —(CH$_2$)$_q$(CHR$^{61}$)$_s$NR$^{33}$R$^{34}$; —(CH$_2$)$_q$(CHR$^{61}$)$_s$OCONR$^{33}$R$^{75}$; —(CH$_2$)$_q$(CHR$^{61}$)$_s$NR$^{20}$CONR$^{33}$R$^{82}$; —(CH$_2$)$_q$(CHR$^{61}$)$_s$COOR$^{57}$; —(CH$_2$)$_q$(CHR$^{61}$)$_s$CONR$^{58}$R$^{59}$; —(CH$_2$)$_q$(CHR$^{61}$)$_s$PO(OR$^{60}$)$_2$; —(CH$_2$)$_q$(CHR$^{61}$)$_s$SO$_2$R$^{62}$; or —(CH$_2$)$_q$(CHR$^{61}$)$_s$C$_6$H$_4$R$^8$;

$R^{14}$ is H; alkyl; alkenyl; —(CH$_2$)$_m$(CHR$^{61}$)$_s$OR$^{55}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_q$(CHR$^{61}$)$_s$COOR$^{57}$; —(CH$_2$)$_q$(CHR$^{61}$)$_s$CONR$^{58}$R$^{59}$; —(CH$_2$)$_q$(CHR$^{61}$)$_s$PO(OR$^{60}$)$_2$; —(CH$_2$)$_q$(CHR$^{61}$)$_s$SOR$^{62}$; or —(CH$_2$)$_q$(CHR$^{61}$)$_s$C$_6$H$_4$R$^8$;

$R^{15}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

$R^{16}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

$R^{17}$ is alkyl; alkenyl; —(CH$_2$)$_q$(CHR$^{61}$)$_s$OR$^{55}$; —(CH$_2$)$_q$(CHR$^{61}$)$_s$SR$^{56}$; —(CH$_2$)$_q$(CHR$^{61}$)$_s$NR$^{33}$R$^{34}$; —(CH$_2$)$_q$(CHR$^{61}$)$_s$OCONR$^{33}$R$^{75}$; —(CH$_2$)$_q$(CHR$^{61}$)$_s$NR$^{20}$CONR$^{33}$R$^{82}$; —(CH$_2$)$_q$(CHR$^{61}$)$_s$COOR$^{57}$; —(CH$_2$)$_q$(CHR$^{61}$)$_s$CONR$^{58}$R$^{59}$; —(CH$_2$)$_q$(CHR$^{61}$)$_s$PO(OR$^{60}$)$_2$; —(CH$_2$)$_q$(CHR$^{61}$)$_s$SO$_2$R$^{62}$; or —(CH$_2$)$_q$(CHR$^{61}$)$_s$C$_6$H$_4$R$^8$;

$R^{18}$ is alkyl; alkenyl; —(CH$_2$)$_p$(CHR$^{61}$)$_s$OR$^{55}$; —(CH$_2$)$_p$(CHR$^{61}$)$_s$SR$^{56}$; —(CH$_2$)$_p$(CHR$^{61}$)$_s$NR$^{33}$R$^{34}$; —(CH$_2$)$_p$(CHR$^{61}$)$_s$OCONR$^{33}$R$^{75}$; —(CH$_2$)$_p$(CHR$^{61}$)$_s$NR$^{20}$CONR$^{33}$R$^{82}$; —(CH$_2$)$_p$(CHR$^{61}$)$_s$COOR$^{57}$; —(CH$_2$)$_p$(CHR$^{61}$)$_s$CONR$^{58}$R$^{59}$; —(CH$_2$)$_p$(CHR$^{61}$)$_s$PO(OR$^{60}$)$_2$; —(CH$_2$)$_p$(CHR$^{61}$)$_s$SO$_2$R$^{62}$; or —(CH$_2$)$_o$(CHR$^{61}$)$_s$C$_6$H$_4$R$^8$;

$R^{19}$ is lower alkyl; —(CH$_2$)$_p$(CHR$^{61}$)$_s$OR$^{55}$; —(CH$_2$)$_p$(CHR$^{61}$)$_s$SR$^{56}$; —(CH$_2$)$_p$(CHR$^{61}$)$_s$NR$^{33}$R$^{34}$; —(CH$_2$)$_p$(CHR$^{61}$)$_s$OCONR$^{33}$R$^{75}$; —(CH$_2$)$_p$(CHR$^{61}$)$_s$NR$^{20}$CONR$^{33}$R$^{82}$; —(CH$_2$)$_p$(CHR$^{61}$)$_s$COOR$^{57}$; —(CH$_2$)$_p$(CHR$^{61}$)$_s$CONR$^{58}$R$^{59}$; —(CH$_2$)$_p$(CHR$^{61}$)$_s$PO(OR$^{60}$)$_2$; —(CH$_2$)$_p$(CHR$^{61}$)$_s$SO$_2$R$^{62}$; or —(CH$_2$)$_o$(CHR$^{61}$)$_s$C$_6$H$_4$R$^8$; or $R^{18}$ and $R^{19}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

$R^{20}$ is H; alkyl; alkenyl; or aryl-lower alkyl;

$R^{21}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

$R^{22}$ is H; alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

$R^{23}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

$R^{24}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

$R^{25}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

$R^{26}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$; or $R^{25}$ and $R^{26}$ taken together can form: —(CH$_2$)$_{2-6}$—; —(CH$_2$)$_r$O(CH$_2$)$_r$—; —(CH$_2$)$_r$S(CH$_2$)$_r$—; or —(CH$_2$)$_r$NR$^{57}$(CH$_2$)$_r$—;

$R^{27}$ is H; alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$ $(CHR^{61})_sCOOR^{57}$; —$(CH_2)_o(CHR^{61})_sCONR^{58}R^{59}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{28}$ is alkyl; alkenyl; —$(CH_2)_o(CHR^{61})_s$—$OR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{29}$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{30}$ is H; alkyl; alkenyl; or aryl-lower alkyl;

$R^{31}$ is H; alkyl; alkenyl; —$(CH_2)_p(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{32}$ is H; lower alkyl; or aryl-lower alkyl;

$R^{33}$ is H; alkyl, alkenyl; —$(CH_2)_m(CHR^{61})_sOR^{55}$; —$(CH_2)_m(CHR^{61})_sNR^{34}R^{63}$; —$(CH_2)_m(CHR^{61})_sOCONR^{75}R^{82}$; —$(CH_2)_m(CHR^{61})_sNR^{20}CONR^{78}R^{82}$; —$(CH_2)_o(CHR^{61})_sCOR^{64}$; —$(CH_2)_o(CHR^{61})_s$—$CONR^{58}R^{59}$, —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{34}$ is H; lower alkyl; aryl, or aryl-lower alkyl;

$R^{33}$ and $R^{34}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{35}$ is H; alkyl; alkenyl; —$(CH_2)_m(CHR^{61})_sOR^{55}$; —$(CH_2)_m(CHR^{61})_sNR^{33}R^{34}$; —$(CH_2)_m(CHR^{61})_sOCONR^{33}R^{75}$; —$(CH_2)_m(CHR^{61})NR^{20}CONR^{33}R^{82}$; —$(CH_2)_p(CHR^{61})_sCOOR^{57}$; —$(CH_2)_p(CHR^{61})_sCONR^{58}R^{59}$; —$(CH_2)_p(CHR^{61})_sPO(OR^{60})_2$; —$(CH_2)_p(CHR^{61})_sSO_2R^{62}$; or —$(CH_2)_p(CHR^{61})_sC_6H_4R^8$;

$R^{36}$ is H, alkyl; alkenyl; —$(CH_2)_o(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_p(CHR^{61})_sCOOR^{57}$; —$(CH_2)_p(CHR^{61})_sCONR^{58}R^{59}$; —$(CH_2)_p(CHR^{61})_sPO(OR^{60})_2$; —$(CH_2)_p(CHR^{61})_sSO_2R^{62}$; or —$(CH_2)_p(CHR^{61})_sC_6H_4R^8$;

$R^{37}$ is H; F; Br; Cl; NO_2; CF_3; lower alkyl; —$(CH_2)_p(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{38}$ is H; F; Br; Cl; NO_2; CF_3; alkyl; alkenyl; —$(CH_2)_p(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{39}$ is H; alkyl; alkenyl; or aryl-lower alkyl;

$R^{40}$ is H; alkyl; alkenyl; or aryl-lower alkyl;

$R^{41}$ is H; F; Br; Cl; NO_2; CF_3; alkyl; alkenyl; —$(CH_2)_p(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{42}$ is H; F; Br; Cl; NO_2; CF_3; alkyl; alkenyl; —$(CH_2)_p(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{43}$ is H; alkyl; alkenyl; —$(CH_2)_m(CHR^{61})_sOR^{55}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{44}$ is alkyl; alkenyl; —$(CH_2)_r(CHR^{61})_sOR^{55}$; —$(CH_2)_r(CHR^{61})_sSR^{56}$; —$(CH_2)_r(CHR^{61})_sNR^{33}R^{34}$; —$(CH_2)_r(CHR^{61})_sOCONR^{33}R^{75}$; —$(CH_2)_r(CHR^{61})_sNR^{20}CONR^{33}R^{82}$; —$(CH_2)_r(CHR^{61})_sCOOR^{57}$; —$(CH_2)_r(CHR^{61})_sCONR^{58}R^{59}$; —$(CH_2)_r(CHR^{61})_sPO(OR^{60})_2$; —$(CH_2)_r(CHR^{61})_sSO_2R^{62}$; or —$(CH_2)_r(CHR^{61})_sC_6H_4R^8$;

$R^{45}$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_s(CHR^{61})_sCONR^{58}R^{59}$; —$(CH_2)_s(CHR^{61})_sPO(OR^{60})_2$; —$(CH_2)_s(CHR^{61})_sSO_2R^{62}$; or —$(CH_2)_s(CHR^{61})_sC_6H_4R^8$;

$R^{46}$ is H; alkyl; alkenyl; or —$(CH_2)_o(CHR^{61})_pC_6H_4R^8$;

$R^{47}$ is H; alkyl; alkenyl; or —$(CH_2)_o(CHR^{61})_sOR^{55}$;

$R^{48}$ is H; lower alkyl; lower alkenyl; or aryl-lower alkyl;

$R^{49}$ is H; alkyl; alkenyl; —$(CHR^{61})_sCOOR^{57}$; $(CHR^{61})_sCONR^{58}R^{59}$; $(CHR^{61})_sPO(OR^{60})_2$; —$(CHR^{61})_sSOR^{62}$; or —$(CHR^{61})_sC_6H_4R^8$;

$R^{50}$ is H; lower alkyl; or aryl-lower alkyl;

$R^{51}$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_pPO(OR^{60})_2$; —$(CH_2)_p(CHR^{61})_sSO_2R^{62}$; or —$(CH_2)_p(CHR^{61})_sC_6H_4R^8$;

$R^{52}$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_pPO(OR^{60})_2$; —$(CH_2)_p(CHR^{61})_sSO_2R^{62}$; or —$(CH_2)_p(CHR^{61})_sC_6H_4R^8$;

$R^{53}$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_pPO(OR^{60})_2$; —$(CH_2)_p(CHR^{61})_sSO_2R^{62}$; or —$(CH_2)_p(CHR^{61})_sC_6H_4R^8$;

$R^{54}$ is H; alkyl; alkenyl; —$(CH_2)_m(CHR^{61})_sOR^{55}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})COOR^{57}$; —$(CH_2)_o(CHR^{61})_sCONR^{58}R^{59}$; or —$(CH_2)_o(CHR^{61})_sC_6H_4R^8$;

$R^{55}$ is H; lower alkyl; lower alkenyl; aryl-lower alkyl; —$(CH_2)_m(CHR^{61})_sOR^{57}$; —$(CH_2)_m(CHR^{61})_sNR^{34}R^{63}$;

—(CH$_2$)$_m$(CHR$^{61}$)$_s$OCONR$^{75}$R$^{82}$; —(CH$_2$)$_m$(CHR$^{61}$)$_s$NR$^{20}$CONR$^{78}$R$^{82}$; —(CH$_2$)$_o$(CHR$^{61}$)$_s$—COR$^{64}$; —(CH$_2$)$_o$(CHR$^{61}$)COOR$^{57}$; or —(CH$_2$)$_o$(CHR$^{61}$)$_s$CONR$^{58}$R$^{59}$;

R$^{56}$ is H; lower alkyl; lower alkenyl; aryl-lower alkyl; —(CH$_2$)$_m$(CHR$^{61}$)$_s$OR$^{57}$; —(CH$_2$)$_m$(CHR$^{61}$)$_s$NR$^{34}$R$^{63}$; —(CH$_2$)$_m$(CHR$^{61}$)$_s$OCONR$^{75}$R$^{82}$; —(CH$_2$)$_m$(CHR$^{61}$)$_s$NR$^{20}$CONR$^{78}$R$^{82}$; —(CH$_2$)$_o$(CHR$^{61}$)$_s$—COR$^{64}$; or —(CH$_2$)$_o$(CHR$^{61}$)$_s$CONR$^{58}$R$^{59}$;

R$^{57}$ is H; lower alkyl; lower alkenyl; aryl lower alkyl; or heteroaryl lower alkyl;

R$^{58}$ is H; lower alkyl; lower alkenyl; aryl; heteroaryl; aryl-lower alkyl; or heteroaryl-lower alkyl;

R$^{59}$ is H; lower alkyl; lower alkenyl; aryl; heteroaryl; aryl-lower alkyl; or heteroaryl-lower alkyl; or R$^{58}$ and R$^{59}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{60}$ is H; lower alkyl; lower alkenyl; aryl; or aryl-lower alkyl;

R$^{61}$ is alkyl; alkenyl; aryl; heteroaryl; aryl-lower alkyl; heteroaryl-lower alkyl; —(CH$_2$)$_m$OR$^{55}$; —(CH$_2$)$_m$NR$^{33}$R$^{34}$; —(CH$_2$)$_m$OCONR$^{75}$R$^{82}$; —(CH$_2$)$_m$NR$^{20}$CONR$^{78}$R$^{82}$; —(CH$_2$)$_o$COOR$^{37}$; —(CH$_2$)$_o$NR$^{58}$R$^{59}$; or —(CH$_2$)$_o$PO(COR$^{60}$)$_2$;

R$^{62}$ is lower alkyl; lower alkenyl; aryl, heteroaryl; or aryl-lower alkyl;

R$^{63}$ is H; lower alkyl; lower alkenyl; aryl; heteroaryl; aryl-lower alkyl; heteroaryl-lower alkyl; —COR$^{64}$; —COOR$^{57}$; —CONR$^{58}$R$^{59}$; —SO$_2$R$^{62}$; or —PO(OR$^{60}$)$_2$;

R$^{34}$ and R$^{63}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{64}$ is H; lower alkyl; lower alkenyl; aryl; heteroaryl; aryl-lower alkyl; heteroaryl-lower alkyl; —(CH$_2$)$_p$(CHR$^{61}$)$_s$OR$^{65}$; —(CH$_2$)$_p$(CHR$^{61}$)$_s$SR$^{66}$; or —(CH$_2$)$_p$(CHR$^{61}$)$_s$NR$^{34}$R$^{63}$; —(CH$_2$)$_p$(CHR$^{61}$)$_s$OCONR$^{75}$R$^{82}$; —(CH$_2$)$_p$(CHR$^{61}$)$_s$NR$^{20}$CONR$^{78}$R$^{82}$;

R$^{65}$ is H; lower alkyl; lower alkenyl; aryl, aryl-lower alkyl; heteroaryl-lower alkyl; —COR$^{57}$; —COOR$^{57}$; or —CONR$^{58}$R$^{59}$;

R$^{66}$ is H; lower alkyl; lower alkenyl; aryl; aryl-lower alkyl; heteroaryl-lower alkyl; or —CONR$^{58}$R$^{59}$;

m is 2-4; o is 0-4; p is 1-4; q is 0-2; r is 1 or 2; s is 0 or 1;

Z is a chain of 12 α-amino acid residues, the positions of said amino acid residues in said chain being counted starting from the N-terminal amino acid, whereby these amino acid residues are, depending on their position in the chain, Gly, or Pro, or of formula -A-CO—, or of formula —B—CO—, or of one of the types C: —NR$^{20}$CH(R$^{72}$)CO—;
D: —NR$^{20}$CH(R$^{73}$)CO—;
E: —NR$^{20}$CH(R$^{74}$)CO—;
F: —NR$^{20}$CH(R$^{84}$)CO—; and
H: —NR$^{20}$—CH(CO—)—(CH$_2$)$_{4-7}$—CH(CO—)—NR$^{20}$—; —NR$^{20}$—CH(CO—)—(CH$_2$)$_p$SS(CH$_2$)$_p$—CH(CO—)—NR$^{20}$—; —NR$^{20}$—CH(CO—)—(—(CH$_2$)$_p$NR$^{20}$CO(CH$_2$)$_p$—CH(CO—)—NR$^{20}$—; and —NR$^{20}$—CH(CO—)—(—(CH$_2$)$_p$NR$^{20}$CONR$^{20}$(CH$_2$)$_p$—CH(CO—)—NR$^{20}$—;

I: —NR$^{86}$CH$_2$CO—;
K: —NR$^{87}$CH$_2$CO—;

R$^{71}$ is H; lower alkyl; lower alkenyl; —(CH$_2$)$_p$(CHR$^{61}$)$_s$OR$^{75}$; —(CH$_2$)$_p$(CHR$^{61}$)$_s$SR$^{75}$; —(CH$_2$)$_p$(CHR$^{61}$)$_s$NR$^{33}$R$^{34}$; —(CH$_2$)$_p$(CHR$^{61}$)$_s$OCONR$^{33}$R$^{75}$; —(CH$_2$)$_p$(CHR$^{61}$)$_s$NR$^{20}$CONR$^{33}$R$^{82}$; —(CH$_2$)$_o$(CHR$^{61}$)$_s$COOR$^{75}$; —(CH$_2$)$_p$CONR$^{58}$R$^{59}$; —(CH$_2$)$_p$PO(OR$^{62}$)$_2$; —(CH$_2$)$_p$SO$_2$R$^{62}$; or —(CH$_2$)$_o$C$_6$R$^{67}$R$^{68}$R$^{69}$R$^{70}$R$^{76}$;

R$^{72}$ is H, lower alkyl; lower alkenyl; —(CH$_2$)$_p$(CHR$^{61}$)$_s$OR$^{85}$; or —(CH$_2$)$_p$(CHR$^{61}$)$_s$SR$^{85}$;

R$^{73}$ is —(CH$_2$)$_o$R$^{77}$; —(CH$_2$)$_r$O(CH$_2$)$_o$R$^{77}$; —(CH$_2$)$_r$S(CH$_2$)$_o$R$^{77}$; or —(CH$_2$)$_r$NR$^{20}$(CH$_2$)$_o$R$^{77}$;

R$^{74}$ is —(CH$_2$)$_p$NR$^{78}$R$^{79}$; —(CH$_2$)$_p$NR$^{77}$R$^{80}$; —(CH$_2$)$_p$(C(=NR$^{80}$)NR$^{78}$R$^{79}$; —(CH$_2$)$_p$C(=NOR$^{50}$)NR$^{78}$R$^{79}$; —(CH$_2$)$_p$C(=NNR$^{78}$R$^{79}$)NR$^{78}$R$^{79}$; —(CH$_2$)$_p$NR$^{80}$C(=NR$^{80}$)NR$^{78}$R$^{79}$; —(CH$_2$)$_p$N=C(NR$^{78}$R$^{80}$)NR$^{79}$R$^{80}$; —(CH$_2$)$_p$C$_6$H$_4$NR$^{78}$R$^{79}$; —(CH$_2$)$_p$C$_6$H$_4$NR$^{77}$R$^{80}$; —(CH$_2$)$_p$C$_6$H$_4$C(=NR$^{80}$)NR$^{78}$R$^{79}$; —(CH$_2$)$_p$C$_6$H$_4$C(=NOR$^{50}$)NR$^{78}$R$^{79}$; —(CH$_2$)$_p$C$_6$H$_4$C(=NNR$^{78}$R$^{79}$)NR$^{78}$R$^{79}$; —(CH$_2$)$_p$C$_6$H$_4$NR$^{80}$C(=NR$^{80}$)NR$^{78}$R$^{79}$; —(CH$_2$)$_p$C$_6$H$_4$N=C(NR$^{78}$R$^{80}$)NR$^{79}$R$^{80}$; —(CH$_2$)$_r$O(CH$_2$)$_m$NR$^{78}$R$^{79}$; —(CH$_2$)$_r$O(CH$_2$)$_m$NR$^{77}$R$^{80}$; —(CH$_2$)$_r$O(CH$_2$)$_p$C(=NR$^{80}$)NR$^{78}$R$^{79}$; —(CH$_2$)$_r$O(CH$_2$)$_p$C(=NOR$^{50}$)NR$^{78}$R$^{79}$; —(CH$_2$)$_r$O(CH$_2$)$_p$C(=NNR$^{78}$R$^{79}$)NR$^{78}$R$^{79}$; —(CH$_2$)$_r$O(CH$_2$)$_m$NR$^{80}$C(=NR$^{80}$)NR$^{78}$R$^{79}$; —(CH$_2$)$_r$O(CH$_2$)$_m$N=C(NR$^{78}$R$^{80}$)NR$^{79}$R$^{80}$; —(CH$_2$)$_r$O(CH$_2$)$_p$C$_6$H$_4$CNR$^{78}$R$^{79}$; —(CH$_2$)$_r$O(CH$_2$)$_p$C$_6$H$_4$C(=NR$^{80}$)NR$^{78}$R$^{79}$; —(CH$_2$)$_r$O(CH$_2$)$_p$C$_6$H$_4$C(=NOR$^{50}$)NR$^{78}$R$^{79}$; —(CH$_2$)$_r$O(CH$_2$)$_p$C$_6$H$_4$C(=NNR$^{78}$R$^{79}$)NR$^{78}$R$^{79}$; —(CH$_2$)$_r$O(CH$_2$)$_p$C$_6$H$_4$NR$^{80}$C(=NR$^{80}$)NR$^{78}$R$^{79}$; —(CH$_2$)$_r$S(CH$_2$)$_m$NR$^{78}$R$^{79}$; —(CH$_2$)$_r$S(CH$_2$)$_m$NR$^{77}$R$^{80}$; —(CH$_2$)$_r$S(CH$_2$)$_p$C(=NR$^{80}$)NR$^{78}$R$^{79}$; —(CH$_2$)$_r$S(CH$_2$)$_p$C(=NOR$^{50}$)NR$^{78}$R$^{79}$; —(CH$_2$)$_r$S(CH$_2$)$_p$C(=NNR$^{78}$R$^{79}$)NR$^{78}$R$^{79}$; —(CH$_2$)$_r$S(CH$_2$)$_m$NR$^{80}$C(=NR$^{80}$)NR$^{78}$R$^{79}$; —(CH$_2$)$_r$S(CH$_2$)$_m$N=C(NR$^{78}$R$^{80}$)NR$^{79}$R$^{80}$; —(CH$_2$)$_r$S(CH$_2$)$_p$C$_6$H$_4$CNR$^{78}$R$^{79}$; —(CH$_2$)$_r$S(CH$_2$)$_p$C$_6$H$_4$C(=NR$^{80}$)NR$^{78}$R$^{79}$; —(CH$_2$)$_r$S(CH$_2$)$_p$C$_6$H$_4$C(=NOR$^{50}$)NR$^{78}$R$^{79}$; —(CH$_2$)$_r$S(CH$_2$)$_p$C$_6$H$_4$C(=NNR$^{78}$R$^{79}$)NR$^{78}$R$^{79}$; —(CH$_2$)$_r$S(CH$_2$)$_p$C$_6$H$_4$NR$^{80}$C(=NR$^{80}$)NR$^{78}$R$^{79}$; —(CH$_2$)$_p$NR$^{80}$COR$^{64}$; —(CH$_2$)$_p$NR$^{80}$COR$^{77}$; —(CH$_2$)$_p$NR$^{80}$CONR$^{78}$R$^{79}$; or —(CH$_2$)$_p$C$_6$H$_4$NR$^{80}$CONR$^{78}$R$^{79}$;

R$^{75}$ is lower alkyl; lower alkenyl; or aryl-lower alkyl;

R$^{33}$ and R$^{75}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{75}$ and R$^{82}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{76}$ is H; lower alkyl; lower alkenyl; aryl-lower alkyl; —(CH$_2$)$_o$OR$^{72}$; —(CH$_2$)$_o$SR$^{72}$; —(CH$_2$)$_o$NR$^{33}$R$^{34}$; —(CH$_2$)$_o$OCONR$^{33}$R$^{75}$; —(CH$_2$)$_o$NR$^{20}$CONR$^{33}$R$^{82}$; —(CH$_2$)$_o$COOR$^{75}$; —(CH$_2$)$_o$CONR$^{58}$R$^{59}$; —(CH$_2$)$_p$PO(OR$^{60}$)$_2$; —(CH$_2$)$_o$SO$_2$R$^{62}$; or —(CH$_2$)$_o$COR$^{64}$;

R$^{77}$ is —C$_6$R$^{67}$R$^{68}$R$^{69}$R$^{70}$R$^{76}$; or a heteroaryl group of one of the formulae

H1

H2

H3

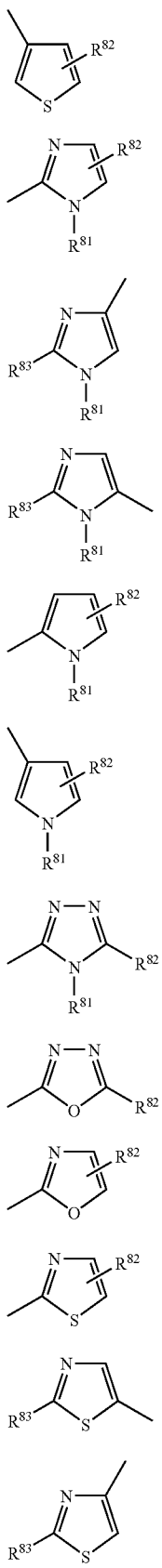
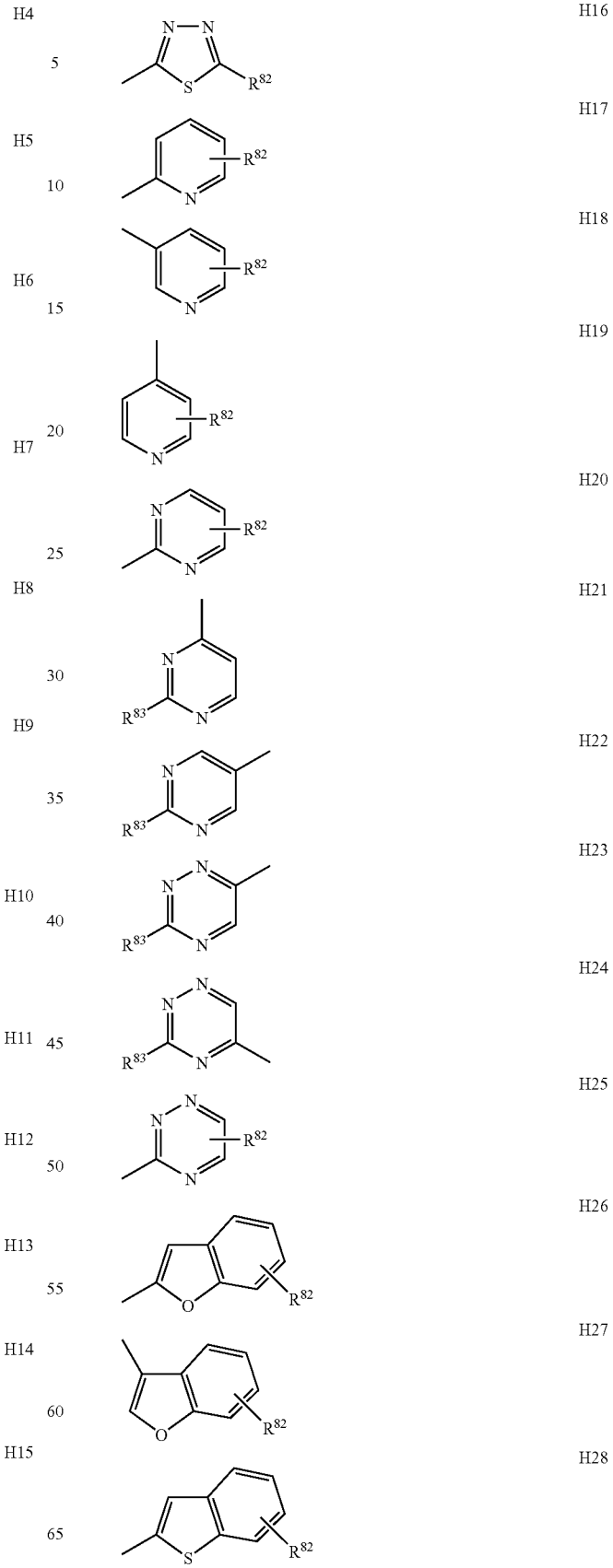

-continued
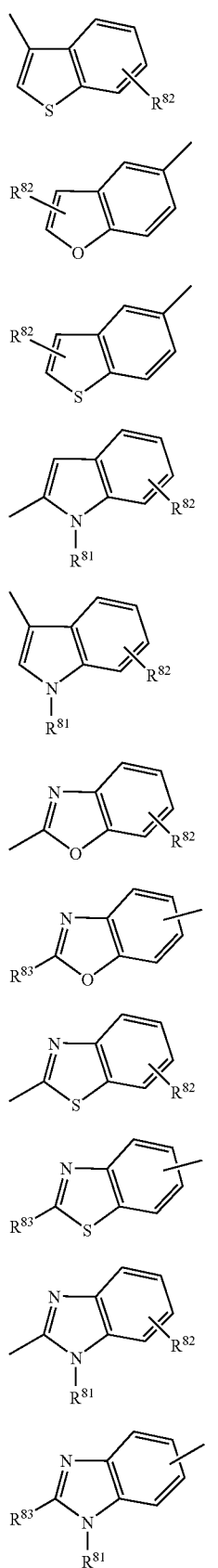
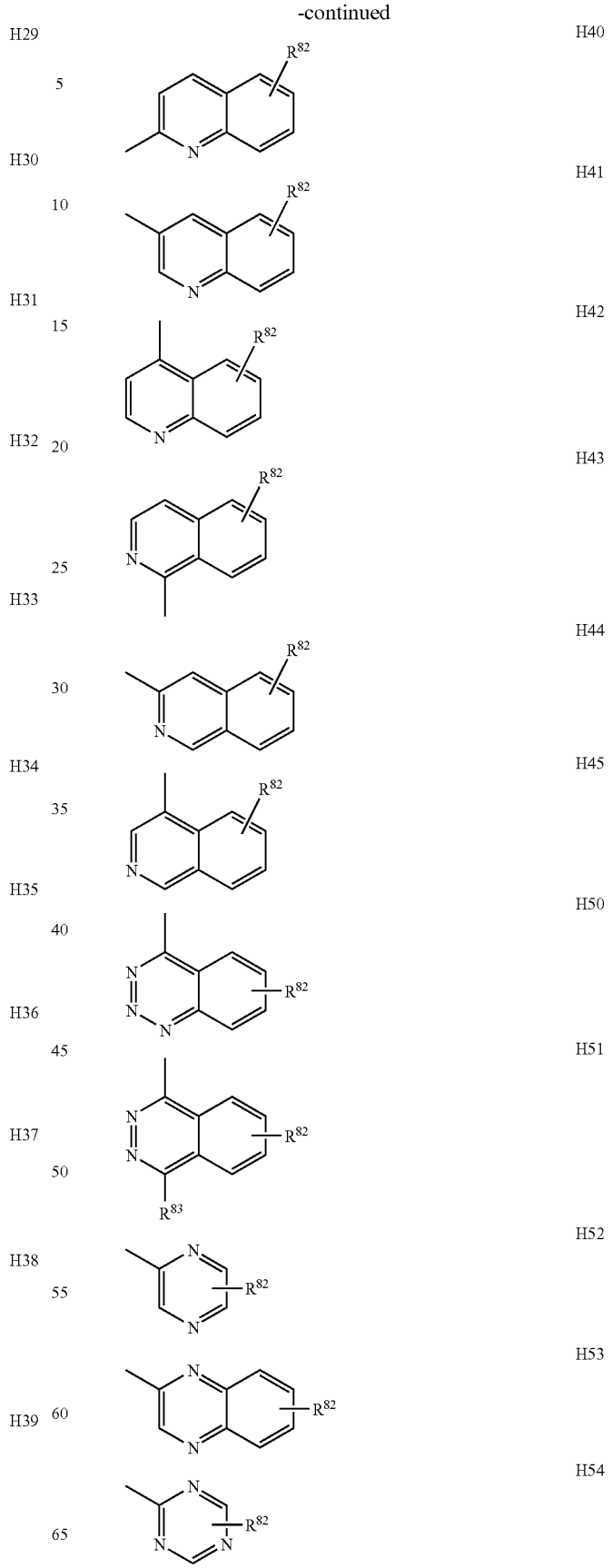

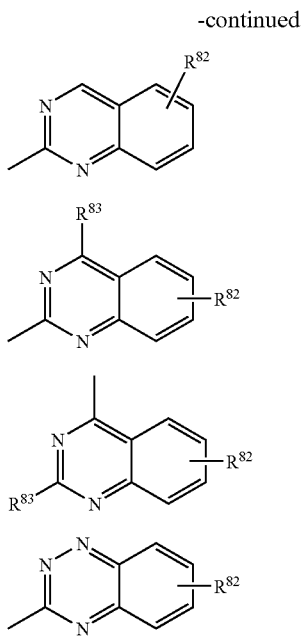

$R^{78}$ is H; lower alkyl; aryl; or aryl-lower alkyl;
$R^{78}$ and $R^{82}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;
$R^{79}$ is H; lower alkyl; aryl; or aryl-lower alkyl; or
$R^{78}$ and $R^{79}$, taken together, can be —$(CH_2)_{2-7}$—; —$(CH_2)_2O(CH_2)_2$—; or —$(CH_2)_2NR^{57}(CH_2)_2$—;
$R^{80}$ is H; or lower alkyl;
$R^{81}$ is H; lower alkyl; or aryl-lower alkyl;
$R^{82}$ is H; lower alkyl; aryl; heteroaryl; or aryl-lower alkyl;
$R^{33}$ and $R^{82}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;
$R^{83}$ is H; lower alkyl; aryl; or —$NR^{78}R^{79}$;
$R^{84}$ is —$(CH_2)_m(CHR^{61})_sOR^{78}$; —$(CH_2)_m(CHR^{61})_sSR^{78}$; —$(CH_2)_pCONR^{78}R^{79}$; —$(CH_2)_pNR^{80}CONR^{78}R^{79}$; —$(CH_2)_pC_6H_4CONR^{78}R^{79}$; or —$(CH)_pC_6H_4NR^{80}CONR^{78}R^{79}$;
$R^{85}$ is lower alkyl; or lower alkenyl;
$R^{86}$ is $R^{74}$; —$[(CH_2)_u—X]_t—(CH_2)_vNR^{78}R^{79}$; —$[(CH_2)_u—X]_t—(CH_2)_v—C(=NR^{80})NR^{78}R^{79}$; X is —O—, —$NR^{20}$—, —S—, —OCOO—, u is 1-3, t is 1-6, v is 1-3;
$R^{87}$ is $R^{84}$; —$[(CH_2)_u—X]_t—(CH_2)_vOR^{78}$, —$[(CH_2)_u—X]_t—(CH_2)_v—CONR^{78}R^{79}$, —$[(CH_2)_u—X]_t—(CH_2)_v—NR^{80}CONR^{78}R^{79}$, —$[(CH_2)_u—X]_t—(CH_2)_vSR^{78}$; X is —O—, —$NR^{20}$—, —S—, —OCOO—, u is 1-3, t is 1-6, v is 1-3;

with the proviso that in said chain of 12 α-amino acid residues Z the amino acid residues in positions 1 to 12 are:
P1: of type C or of type D or of type E or of type F, or the residue is Pro;
P2: of type E or of type D;
P3: of type C, or the residue is Pro;
P4: of type E or of type F or of type I or of type K;
P5: of type E or of type D or or of type C or of type I or of type K or of type F, or the residue is Gly or Pro;
P6: of type E or of type F or of formula -A-CO—, or of type I or of type K or of type D, or the residue is Gly;
P7: of type E or of type F or of type I or of type C or of formula —B—CO—;
P8: of type D or of type C, or the residue is Pro;
P9: of type E or of type D or of type F;
P10: of type D or of type C or the residue is Pro;
P11: of type E or of type D or of type C; and
P12: of type C or of type D or of type E or of type F, or the residue is Pro; or
P4 and P9 and/or P2 and P11, taken together, can form a group of type H; and at P6 and P7 also D-isomers being possible;
with the further proviso that said chain of 12 α-amino acid residues contains at least one residue of type I or of type K;

and pharmaceutically acceptable salts thereof.

In accordance with the present invention these β-hairpin peptidomimetics can be prepared by a process which comprises (a) coupling an appropriately functionalized solid support with an appropriately N-protected derivative of that amino acid which in the desired end-product is in position 5, 6 or 7, any functional group which may be present in said N-protected amino acid derivative being likewise appropriately protected;

(b) removing the N-protecting group from the product thus obtained;

(c) coupling the product thus obtained with an appropriately N-protected derivative of that amino acid or which in the desired end-product is one position nearer the N-terminal amino acid residue, any functional group which may be present in said N-protected amino acid derivative being likewise appropriately protected;

(d) removing the N-protecting group from the product thus obtained;

(e) repeating steps (c) and (d) until the N-terminal amino acid residue has been introduced;

(f) coupling the product thus obtained with a compound of the general formula

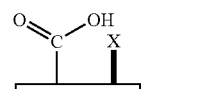 II wherein

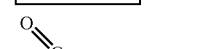

is as defined above and X is an N-protecting group or, if

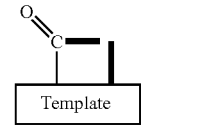

is to be group (a1) or (a2), above, alternatively (fa) coupling the product obtained in step (e) with an appropriately N-protected derivative of an amino acid of the general formula

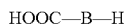 III or

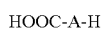 IV wherein B and A are as defined above, any functional group which may be present in said N-protected amino acid derivative being likewise appropriately protected;

(fb) removing the N-protecting group from the product thus obtained; and (fc) coupling the product thus obtained with an appropriately N-protected derivative of an amino acid of the above general formula IV and, respectively, III, any functional group which may be present in said N-protected amino acid derivative being likewise appropriately protected;

(g) removing the N-protecting group from the product obtained in step (f) or (fc);

(h) coupling the product thus obtained with an appropriately N-protected derivative of that amino acid which in the desired end-product is in position 12, any functional group which may be present in said N-protected amino acid derivative being likewise appropriately protected;

(i) removing the N-protecting group from the product thus obtained;

(j) coupling the product thus obtained with an appropriately N-protected derivative of that amino acid which in the desired end-product is one position farther away from position 12, any functional group which may be present in said N-protected amino acid derivative being likewise appropriately protected;

(k) removing the N-protecting group from the product thus obtained;

(l) repeating steps (j) and (k) until all amino acid residues have been introduced;

(m) if desired, selectively deprotecting one or several protected functional group(s) present in the molecule and appropriately substituting the reactive group(s) thus liberated;

(o) detaching the product thus obtained from the solid support;

(p) cyclizing the product cleaved from the solid support;

(q) if desired, forming one or two interstrand linkage(s) between side-chains of appropriate amino acid residues at opposite positions of the β-strand region;

(r) removing any protecting groups present on functional groups of any members of the chain of amino acid residues and, if desired, any protecting group(s) which may in addition be present in the molecule;

(s) if desired modify any functional group of the chain of amino acid residues; and (t) if desired, converting the product thus obtained into a pharmaceutically acceptable salt or converting a pharmaceutically acceptable, or unacceptable, salt thus obtained into the corresponding free compound of formula I or into a different, pharmaceutically acceptable, salt.

Alternatively, the peptidomimetics of the present invention can be prepared by (a') coupling an appropriately functionalized solid support with a compound of the general formula

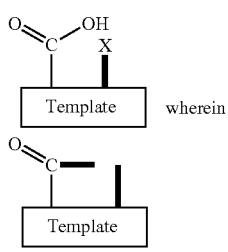

II wherein is as defined above and X is an N-protecting group or, if

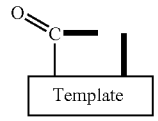

is to be group (a1) or (a2), above, alternatively (a'a) coupling said appropriately functionalized solid support with an appropriately N-protected derivative of an amino acid of the general formula

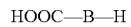 HOOC—B—H   III or

 HOOC-A-H   IV wherein B and A are as defined above, any functional group which may be present in said N-protected amino acid derivative being likewise appropriately protected;

(a'b) removing the N-protecting group from the product thus obtained; and (a'c) coupling the product thus obtained with an appropriately N-protected derivative of an amino acid of the above general formula IV and, respectively, III, any functional group which may be present in said N-protected amino acid derivative being likewise appropriately protected;

(b') removing the N-protecting group from the product obtained in step (a') or (a'c);

(c') coupling the product thus obtained with an appropriately N-protected derivative of that amino acid which in the desired end-product is one position nearer the N-terminal amino acid residue, any functional group which may be present in said N-protected amino acid derivative being likewise appropriately protected;

(d') removing the N-protecting group from the product thus obtained;

(e') coupling the product thus obtained with an appropriately N-protected derivative of that amino acid which in the desired end-product is one position farther away from position 12, any functional group which may be present in said N-protected amino acid derivative being likewise appropriately protected;

(f') removing the N-protecting group from the product thus obtained;

(g') repeating steps (e') and (f') until all amino acid residues have been introduced;

(h') if desired, selectively deprotecting one or several protected functional group(s) present in the molecule and appropriately substituting the reactive group(s) thus liberated;

(i') detaching the product thus obtained from the solid support;

(j') cyclizing the product cleaved from the solid support;

(k') if desired forming one or two interstrand linkage(s) between side-chains of appropriate amino acid residues at opposite positions of the β-strand region;

(l') removing any protecting groups present on functional groups of any members of the chain of amino acid residues and, if desired, any protecting group(s) which may in addition be present in the molecule;

(m') if desired guanidinylating any side chain-amino group present in the chain of amino acid residues; and (n') if desired, converting the product thus obtained into a pharmaceutically acceptable salt or converting a pharmaceutically acceptable, or unacceptable, salt thus obtained into the corresponding free compound of formula I or into a different, pharmaceutically acceptable, salt.

Introducing an amino acid residue of type I or K can, alternatively, be effected by coupling with a leaving group-containing acetylating agent, such as bromo, chloro or iodo acetic acid, followed by nucleophilic displacement with an amine of the formula $H_2NR^{87}$ and, respectively, $H_2NR^{87}$ which, if necessary, is appropriately protected.

The peptidomimetics of the present invention can also be enantiomers of the compounds of formula I. These enantiomers can be prepared by a modification of the above processes in which enantiomers of all chiral starting materials are used.

As used in this description, the term "alkyl", taken alone or in combinations, designates saturated, straight-chain or branched hydrocarbon radicals having up to 24, preferably up to 12, carbon atoms. Similarly, the term "alkenyl" designates straight chain or branched hydrocarbon radicals having up to 24, preferably up to 12, carbon atoms and containing at least one or, depending on the chain length, up to four olefinic double bonds. The term "lower" designates radicals and compounds having up to 6 carbon atoms. Thus, for example, the term "lower alkyl" designates saturated, straight-chain or branched hydrocarbon radicals having up to 6 carbon atoms, such as methyl, ethyl, n-propyl, isopropyl, n-butyl, sec.-butyl, isobutyl, tert.-butyl and the like.

The term "aryl" designates aromatic carbocyclic hydrocarbon radicals containing one or two six-membered rings, such as phenyl or naphthyl, which may be substituted by up to three substituents such as Br, Cl, F, $CF_3$, $NO_2$, OH, $NH_2$, lower alkyl or lower alkenyl. The term "heteroaryl" designates aromatic heterocyclic radicals containing one or two five- and/or six-membered rings, at least one of them containing up to three heteroatoms selected from the group consisting of O, S and N and said ring(s) being optionally substituted; representative examples of such optionally substituted heteroaryl radicals are indicated hereinabove in connection with the definition of $R^{77}$.

The structural element -A-CO— designates amino acid building blocks which in combination with the structural element —B—CO— form templates (a1) and (a2). Templates (a) through (p) constitute building blocks which have an N-terminus and a C-terminus oriented in space in such a way that the distance between those two groups may lie between 4.0-5.5 Å. A peptide chain Z is linked to the C-terminus and the N-terminus of the templates (a) through (p) via the corresponding N- and C-termini so that the template and the chain form a cyclic structure such as that depicted in formula I. In a case as here where the distance between the N- and C-termini of the template lies between 4.0-5.5 Å the template will induce the H-bond network necessary for the formation of a β-hairpin conformation in the peptide chain Z. Thus template and peptide chain form a β-hairpin mimetic.

The β-hairpin conformation is highly relevant for the antibiotic activity of the β-hairpin mimetics of the present invention. The β-hairpin stabilizing conformational properties of the templates (a) through (p) play a key role not only for antibiotic activity but also for the synthesis process defined hereinabove, as incorporation of the templates near the middle or at the beginning of the linear protected peptide precursors enhance cyclization yields.

Building blocks A1-A69 belong to a class of amino acids wherein the N-terminus is a secondary amine forming part of a ring. Among the genetically encoded amino acids only proline falls into this class. The configuration of building block A1 through A69 is (D), and they are combined with a building block —B—CO— of (L)-configuration. Preferred combinations for templates (a1) are—$^D$A1-CO-$^L$B—CO— to $^D$A69-CO-$^L$B—CO—. Thus, for example, $^D$Pro-$^L$Pro constitutes the prototype of templates (a1). Less preferred, but possible are combinations where templates (a2) are—$^L$A1-CO-$^D$B—CO— to $^L$A69-CO-$^D$B—CO—. Thus, for example, $^L$Pro-$^D$Pro constitutes a less preferred prototype of template (a2).

It will be appreciated that building blocks -A1-CO— to -A69-CO— in which A has (D)-configuration, are carrying a group $R^1$ at the α-position to the N-terminus. The preferred values for $R^1$ are H and lower alkyl with the most preferred values for $R^1$ being H and methyl. It will be recognized by those skilled in the art, that A1-A69 are shown in (D)-configuration which, for $R^1$ being H and methyl, corresponds to the (R)-configuration. Depending on the priority of other values for $R^1$ according to the Cahn, Ingold and Prelog-rules, this configuration may also have to be expressed as (S).

In addition to $R^1$ building blocks -A1-CO— to -A69-CO— can carry an additional substituent designated as $R^2$ to $R^{17}$. This additional substituent can be H, and if it is other than H, it is preferably a small to medium-sized aliphatic or aromatic group. Examples of preferred values for $R^2$ to $R^{17}$ are:

$R^2$: H; lower alkyl; lower alkenyl; $(CH_2)_mOR^{55}$ (where $R^{55}$: lower alkyl; or lower alkenyl); $(CH_2)_mSR^{56}$ (where $R^{56}$: lower alkyl; or lower alkenyl); $(CH_2)_mNR^{33}R^{34}$ (where $R^{33}$: lower alkyl; or lower alkenyl; $R^{34}$: H; or lower alkyl; $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; $R^{57}$: H; or lower alkyl); $(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^3$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl;

$R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); $(CH_2)_oPO(OR^{60})_2$ (where $R^{60}$: lower alkyl; or lower alkenyl); —$CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^4$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^5$: lower alkyl; lower alkenyl; —$(CH_2)_oOR^5$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; $R^{57}$: where H; or lower alkyl); $(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); $(CH_2)_oN(R^{20})COR^{64}$ (where: $R^{20}$: H; or lower alkyl; $R^{64}$: alkyl; alkenyl; aryl; and aryl-lower alkyl; heteroaryl-lower alkyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^6$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^7$: lower alkyl; lower alkenyl; —$(CH_2)_qOR^{55}$ (where $R^{55}$: lower alkyl; or lower alkenyl); —$(CH_2)_qSR^{56}$ (where $R^{56}$: lower alkyl; or lower alkenyl); —$(CH_2)_qNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qN(R^{20})COR^{64}$ (where: $R^{20}$: H; or lower alkyl; $R^{64}$: lower alkyl; or lower alkenyl); —$(CH_2)_rCOOR^{57}$ (where $R^{57}$: lower alkyl; or lower alkenyl); —$(CH_2)_qCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_rPO(OR^{60})_2$ (where $R^{60}$: lower alkyl; or lower alkenyl); $(CH_2)_sSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^8$: H; F; Cl; $CF_3$; lower alkyl; lower alkenyl; —$(CH_2)_oOR^{55}$ (where $R^{55}$: lower alkyl; or lower alkenyl); $(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^9$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{10}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{11}$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{12}$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form:

—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$N(R$^{20}$)COR$^{64}$ (where: R$^{20}$: H; or lower alkyl; R$^{64}$: lower alkyl; or lower alkenyl); —(CH$_2$)$_r$COOR$^{57}$ (where R$^{57}$: lower alkyl; or lower alkenyl); —(CH$_2$)$_r$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_r$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{13}$: lower alkyl; lower alkenyl; —(CH$_2$)$_q$OR$^{55}$ (where R$^{55}$: lower alkyl; or lower alkenyl); —(CH$_2$)$_q$SR$^{56}$ (where R$^{56}$: lower alkyl; or lower alkenyl); —(CH$_2$)$_q$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_q$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_q$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_q$N(R$^{20}$)COR$^{64}$ (where: R$^{20}$: H; or lower alkyl; R$^{64}$: lower alkyl; or lower alkenyl); —(CH$_2$)$_r$COO$^{57}$ (where R$^{57}$: lower alkyl; or lower alkenyl); —(CH$_2$)$_q$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_r$PO(OR$^{60}$)$_2$ (where R$^{60}$: lower alkyl; or lower alkenyl); —(CH$_2$)$_r$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{14}$: H; lower alkyl; lower alkenyl; —(CH$_2$)$_m$OR$^{55}$ (where R$^{55}$: lower alkyl; or lower alkenyl); —(CH$_2$)$_m$SR$^{56}$ (where R$^{56}$: lower alkyl; or lower alkenyl); —(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$N(R$^{20}$)COR$^{64}$ (where: R$^{20}$: H; lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); —(CH$_2$)$_q$C$_6$H$_4$R$^8$ (where R$^8$: H; F; Cl; CF$_3$; lower alkyl; lower alkenyl; or lower alkoxy).

R$^{15}$: lower alkyl; lower alkenyl; —(CH$_2$)$_o$OR$^5$s (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$NR$^{20}$CONR$^{33}$R$^{82}$ (where R$^{20}$: H; or lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); (CH$_2$)$_o$N(R$^{20}$)COR$^{64}$ (where: R$^{20}$: H; or lower alkyl; R$^{64}$: lower alkyl; or lower alkenyl); particularly favoured are NR$^{20}$CO lower alkyl (R$^{20}$=H; or lower alkyl); —(CH$_2$)$_o$COOR$^{57}$ (Where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{16}$: lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{17}$: lower alkyl; lower alkenyl; —(CH$_2$)$_q$OR$^{55}$ (where R$^{55}$: lower alkyl; or lower alkenyl); —(CH$_2$)$_q$SR$^{56}$ (where R$^{56}$: lower alkyl; or lower alkenyl); —(CH$_2$)$_q$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_q$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_q$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_q$N(R$^{20}$)COR$^{64}$ (where: R$^{20}$: H; or lower alkyl; R$^{64}$: lower alkyl; or lower alkenyl); —(CH$_2$)$_r$COOR$^{57}$ (where R$^{57}$: lower alkyl; or lower alkenyl); —(CH$_2$)$_q$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_r$PO(OR$^{60}$)$_2$ (where R$^{60}$: lower alkyl; or lower alkenyl); —(CH$_2$)$_r$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

Among the building blocks A1 to A69 the following are preferred: A5 with R$^2$ being H, A8, A22, A25, A38 with R$^2$ being H, A42, A47, and A50. Most preferred are building blocks of type A8':

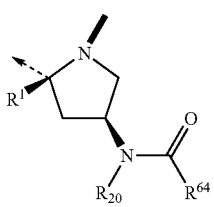

A8' wherein R$^{20}$ is H or lower alkyl; and R$^{64}$ is alkyl; alkenyl; aryl; aryl-lower alkyl; or heteroaryl-lower alkyl; especially those wherein R$^{64}$ is n-hexyl (A8'-1); n-heptyl (A8'-2); 4-(phenyl) benzyl (A8'-3); diphenylmethyl (A8'-4); 3-amino-propyl (A8'-5); 5-amino-pentyl (A8'-6); methyl (A8'-7); ethyl (A8'-8); isopropyl (A8'-9); isobutyl (A8'-10); n-propyl (A8'-11); cyclohexyl (A8'-12); cyclohexylmethyl (A8'-13); n-butyl (A8'-14); phenyl (A8'-15); benzyl (A8'-16); (3-indolyl)methyl (A8'-17); 2-(3-indolyl)ethyl (A8'-18); (4-phenyl)phenyl (A8'-19); and n-nonyl (A8'-20).

Building block A70 belongs to the class of open-chained α-substituted α-amino acids, building blocks A71 and A72 to the corresponding β-amino acid analogues and building blocks A73-A104 to the cyclic analogues of A70. Such amino acid derivatives have been shown to constrain small peptides in well defined reverse turn or U-shaped conformations (C. M. Venkatachalam, *Biopolymers,* 1968, 6, 1425-1434; W. Kabsch, C Sander, Biopolymers 1983, 22, 2577). Such building blocks or templates are ideally suited for the stabilization of β-hairpin conformations in peptide loops (D. Obrecht, M. Altorfer, J. A. Robinson, "Novel Peptide Mimetic Building Blocks and Strategies for Efficient Lead Finding", *Adv. Med Chem.* 1999, Vol. 4, 1-68; P. Balaram, "Non-standard amino acids in peptide design and protein engineering", *Curr. Opin. Struct. Biol.* 1992, 2, 845-851; M. Crisma, G. Valle, C. Toniolo, S. Prasad, R. B. Rao, P. Balaram, "β-turn conformations in crystal structures of model peptides containing α,α-disubstituted amino acids", *Biopolymers* 1995, 35, 1-9; V. J. Hruby, F. Al-Obeidi, W. Kazmierski, *Biochem. J.* 1990, 268, 249-262).

It has been shown that both enantiomers of building blocks -A70-CO— to A104-CO— in combination with a building block —B—CO— of L-configuration can efficiently stabilize and induce β-hairpin conformations (D. Obrecht, M. Altorfer, J. A. Robinson, "Novel Peptide Mimetic Building Blocks and Strategies for Efficient Lead Finding", *Adv. Med Chem.* 1999, Vol. 4, 1-68; D. Obrecht, C. Spiegler, P. Schönholzer, K. Müller, H. Heimgartner, F. Stierli, *Helv. Chim. Acta* 1992, 75, 1666-1696; D. Obrecht, U. Bohdal, J. Daly, C. Lehmann, P. Schönholzer, K. Müller, *Tetrahedron* 1995, 51, 10883-10900; D. Obrecht, C. Lehmann, C. Ruffieux, P. Schönholzer, K. Müller, *Helv. Chim. Acta* 1995, 78, 1567-1587; D. Obrecht, U. Bohdal, C. Broger, D. Bur, C. Lehmann, R. Ruffieux, P. Schönholzer, C. Spiegler, *Helv. Chim. Acta* 1995, 78, 563-580; D. Obrecht, H. Karajiannis, C. Lehmann, P. Schönholzer, C. Spiegler, *Helv. Chim. Acta* 1995, 78, 703-714).

Thus, for the purposes of the present invention templates (a1) can also consist of -A70-CO— to A104-CO— where building block A70 to A104 is of either (D)- or (L)-configuration, in combination with a building block —B—CO— of (L)-configuration.

Preferred values for R$^{20}$ in A70 to A104 are H or lower alkyl with methyl being most preferred. Preferred values for R$^{18}$, R$^{19}$ and R$^{21}$-R$^{29}$ in building blocks A70 to A104 are the following:

R$^{18}$: lower alkyl.

R$^{19}$: lower alkyl; lower alkenyl; —(CH$_2$)$_p$OR$^{55}$ (where R$^{55}$: lower alkyl; or lower alkenyl); —(CH$_2$)$_p$SR$^{56}$ (where R$^{56}$: lower alkyl; or lower alkenyl); —(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_p$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$N(R$^{20}$)COR$^{64}$ (where: R$^{20}$: H; or lower alkyl; R$^{64}$: lower alkyl; or lower alkenyl); —(CH$_2$)$_p$COOR$^{57}$ (where R$^{57}$: lower alkyl; or lower alkenyl); —(CH$_2$)$_p$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_p$SO$_2$R$^{62}$ (where R$^{62}$: lower alkyl; or lower alkenyl); or —(CH$_2$)$_o$C$_6$H$_4$R$^8$ (where R$^8$: H; F; Cl; CF$_3$; lower alkyl; lower alkenyl; or lower alkoxy).

R$^{21}$: H; lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl);

—(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); (CH$_2$)$_o$SO$_2$R$^{62}$ (where R$^{62}$: lower alkyl; or lower alkenyl); or (CH$_2$)$_q$C$_6$H$_4$R$^8$ (where R$^8$: H; F; Cl; CF$_3$; lower alkyl; lower alkenyl; or lower alkoxy).

R$^{22}$: lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$N(R$^2$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF; lower alkyl; lower alkenyl; or lower alkoxy).

R$^{23}$: H; lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); particularly favoured are NR$^{20}$CO lower alkyl (R$^{20}$═H; or lower alkyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy);

R$^{24}$: lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$; where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); particularly favoured are NR$^{20}$CO lower alkyl (R$^{20}$═H; or lower alkyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy);

R$^{25}$: H; lower alkyl; lower alkenyl; —(CH$_2$)$_m$OR$^{55}$ (where R$^{55}$: lower alkyl; or lower alkenyl); —(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_m$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O (CH$_2$)$_2$—; —(CH$_2$)$_2$S(CH$_2$)$_2$—; or —(CH$_2$)$_2$NR$^{57}$ (CH$_2$)$_2$—; where R$^{57}$: H; or lower alkyl); —(CH$_2$)$_m$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_m$N(R$^{20}$)COR$^{64}$ (where: R$^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{26}$: H; lower alkyl; lower alkenyl; —$(CH_2)_mOR^{55}$ (where $R^{55}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$(where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

Alternatively, $R^{25}$ and $R^{26}$ taken together can be —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl).

$R^{27}$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{28}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower alkyl or lower alkenyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$(where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{29}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); particularly favored are $NR^{20}CO$ lower-alkyl ($R^{20}$=H; or lower alkyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

For templates (b) to (p), such as (b1) and (c1), the preferred values for the various symbols are the following:

$R^8$: H; F; Cl; $CF_3$; lower alkyl; lower alkenyl; $-(CH_2)_oOR^{55}$ (where $R^{55}$: lower alkyl; or lower alkenyl); $-(CH_2)_oSR^{56}$ (where $R^{56}$: lower alkyl; or lower alkenyl); $-(CH_2)_oNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_o NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^{20}$: H; or lower alkyl.

$R^{30}$: H, methyl.

$R^{31}$: H; lower alkyl; lower alkenyl; $-(CH_2)_pOR^{55}$ (where $R^{55}$: lower alkyl; or lower alkenyl); $-(CH_2)_pNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_pNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_pN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $(-CH_2)_oCONR^{58}R^{59}$ (where $R^{58}$: lower alkyl, or lower alkenyl; and $R^{59}$: H; lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_rC_6H_4R^8$ (where $R^8$: H; F; Cl; $CF_3$; lower alkyl; lower alkenyl; or lower alkoxy); most preferred is $-CH_2CONR^{58}R^{59}$ ($R^{58}$: H; or lower alkyl; $R^{59}$: lower alkyl; or lower alkenyl).

$R^{32}$: H, methyl.

$R^{33}$: lower alkyl; lower alkenyl; $-(CH^2)_mOR^{55}$ (where $R^{55}$: lower alkyl; or lower alkenyl); $-(CH_2)_mNR^{34}R^{63}$ (where $R^{34}$: lower alkyl; or lower alkenyl; $R^{63}$: H; or lower alkyl; or $R^{34}$ and $R^{63}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $(CH_2)_mOCONR^{75}R^{82}$ (where $R^{75}$: lower alkyl; or lower alkenyl; $R^{82}$: H; or lower alkyl; or $R^{75}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mNR^{20}CONR^{78}R^{82}$ (where $R^{20}$: H; or lower lower alkyl; $R^{78}$: H; or lower alkyl; or lower alkenyl; $R^{82}$: H; or lower alkyl; or $R^{78}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl).

$R^{34}$: H; or lower alkyl.

$R^{35}$: H; lower alkyl; lower alkenyl; $-(CH_2)_mOR^{55}$ (where $R^{55}$: lower alkyl; or lower alkenyl); $-(CH_2)_mNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_mN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl).

$R^{36}$: lower alkyl; lower alkenyl; or aryl-lower alkyl.

$R^{37}$: H; lower alkyl; lower alkenyl; $-(CH_2)_pOR^{55}$ (where $R^{55}$: lower alkyl; or lower alkenyl); $-(CH_2)_pNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_pNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_pN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{38}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{78}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{39}$: H; lower alkyl; lower alkenyl; —$(CH_2)_mOR^{55}$ (where $R^{55}$: lower alkyl; or lower alkenyl); —$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl).

$R^{40}$: lower alkyl; lower alkenyl; or aryl-lower alkyl.

$R^{41}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{42}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{43}$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2O$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^2CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{44}$: lower alkyl; lower alkenyl; —$(CH_2)_pOR^{55}$ (where $R^{55}$: lower alkyl; or lower alkenyl); —$(CH_2)_pSR^{56}$ (where $R^{56}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{78}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_oC_6H_4R^8$ (where $R^8$: H; F; Cl; $CF_3$; lower alkyl; lower alkenyl; or lower alkoxy).

$R^{45}$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_sC_6H_4R^8$ (where $R^8$: H; F; Cl; $CF_3$; lower alkyl; lower alkenyl; or lower alkoxy).

$R^{46}$: H; lower alkyl; lower alkenyl; —$(CH_2)_sOR^{55}$ (where $R^{55}$: lower alkyl; or lower alkenyl); —$(CH_2)_sR^{56}$ (where $R^{56}$: lower alkyl; or lower alkenyl); —$(CH_2)_sNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_sOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_sNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S (CH_2)_2$—; or —$(CH_2)_2NR^{57}(CH_2)_2$—; where $R^{57}$: H; or lower alkyl); —$(CH_2)_sN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_sC_6H_4R^8$ (where $R^8$: H; F; Cl; $CF_3$; lower alkyl; lower alkenyl; or lower alkoxy).

$R^{47}$: H; or $OR^{55}$ (where $R^{55}$: lower alkyl; or lower alkenyl).

$R^{48}$: H; or lower alkyl.

$R^{49}$: H; lower alkyl; —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or $(CH_2)_sC_6H_4R^8$ (where $R^8$: H; F; Cl; $CF_3$; lower alkyl; lower alkenyl; or lower alkoxy).

$R^{50}$: H; methyl.

$R^{51}$: H; lower alkyl; lower alkenyl; —$(CH_2)_mOR^{55}$ (where $R^{55}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); $(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl, $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_rC_6H_4R^8$ (where $R^8$: H; F; Cl; $CF_3$; lower alkyl; lower alkenyl; or lower alkoxy).

$R^{52}$: H; lower alkyl; lower alkenyl; —$(CH_2)_mOR^{55}$ (where $R^{55}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_2$—; —$(CH_2)_2O(CH_2)_2$—; —$(CH_2)_2S(CH_2)_2$—; or —$(CH_2)_2NR^{57}(CH_2)_2$—; $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —(CH$_2$)$_p$CONR$^{58}$R$^{59}$ (where R$^{58}$: lower alkyl; or lower alkenyl; and R$^{59}$: H; lower alkyl; or lower alkenyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); or —(CH$_2$)$_r$C$_6$H$_4$R$^8$ (where R$^8$: H; F; Cl; CF$_3$; lower alkyl; lower alkenyl; or lower alkoxy).

R$^{53}$: H; lower alkyl; lower alkenyl; —(CH$_2$)$_m$OR$^{55}$ (where R$^{55}$: lower alkyl; or lower alkenyl); —(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_m$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O (CH$_2$)$_2$—; —(CH$_2$)$_2$S(CH$_2$)$_2$—; or —(CH$_2$)$_2$NR$^{57}$ (CH$_2$)$_2$—; where R$^{57}$: H; or lower alkyl); —(CH$_2$)$_m$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_m$N(R$^{20}$)COR$^{64}$ (where: R$^{20}$: H; or lower alkyl; R64: lower alkyl; or lower alkenyl); —(CH$_2$)$_p$COOR$^{57}$ (where R$^{57}$: lower alkyl; or lower alkenyl); —(CH$_2$)$_p$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O (CH$_2$)$_2$—; —(CH$_2$)$_2$S(CH$_2$)$_2$—; or —(CH$_2$)$_2$NR$^{57}$ (CH$_2$)$_2$—; where R$^{57}$: H; or lower alkyl); or —(CH$_2$)$_r$C$_6$H$_4$R$^8$ (where R$^8$: H; F; Cl; CF$_3$; lower alkyl; lower alkenyl; or lower alkoxy).

R$^{54}$: lower alkyl; lower alkenyl; or aryl-lower alkyl.

Among the building blocks A70 to A104 the following are preferred: A74 with R$^{22}$ being H, A75, A76, A77 with R$^{22}$ being H, A78 and A79.

The building block —B—CO— within template (a1) and (a2) designates an L-amino acid residue. Preferred values for B are: —NR$^{20}$CH(R$^{71}$)— and enantiomers of groups A5 with R$^2$ being H, A8, A22, A25, A38 with R$^2$ being H, A42, A47, and A50. Most preferred are

| | |
|---|---|
| Ala | L-Alanine |
| Arg | L-Arginine |
| Asn | L-Asparagine |
| Cys | L-Cysteine |
| Gln | L-Glutamine |
| Gly | Glycine |
| His | L-Histidine |
| Ile | L-Isoleucine |
| Leu | L-Leucine |
| Lys | L-Lysine |
| Met | L-Methionine |
| Phe | L-Phenylalanine |
| Pro | L-Proline |
| Ser | L-Serine |
| Thr | L-Threonine |
| Trp | L-Tryptophan |
| Tyr | L-Tyrosine |
| Val | L-Valine |
| Cit | L-Citrulline |
| Orn | L-Ornithine |
| tBuA | L-t-Butylalanine |
| Sar | Sarcosine |
| BnGly | N-Benzylglycine |
| Bn(4-OH)Gly | N-4-Hydroxy-benzylglycine |
| t-BuG | L-tert.-Butylglycine |

-continued

| | |
|---|---|
| 4AmPhe | L-para-Aminophenylalanine |
| 3AmPhe | L-meta-Aminophenylalanine |
| 2AmPhe | L-ortho-Aminophenylalanine |
| Phe(mC(NH$_2$)=NH) | L-meta-Amidinophenylalanine |
| Phe(pC(NH$_2$)=NH) | L-para-Amidinophenylalanine |
| Phe(mNHC(NH$_2$)=NH) | L-meta-Guanidinophenylalanine |
| Phe(pNHC(NH$_2$)=NH) | L-para-Guanidinophenylalanine |
| Phg | L-Phenylglycine |
| Cha | L-Cyclohexylalanine |
| C$_4$al | L-3-Cyclobutylalanine |
| C$_5$al | L-3-Cyclopentylalanine |
| Nle | L-Norleucine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4Cl$_2$-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Tic | L-1,2,3,4-Tetrahydroisoquinoline-3-carboxylic acid |
| Thi | L-β-2-Thienylalanine |
| Tza | L-2-Thiazolylalanine |
| Mso | L-Methionine sulfoxide |
| AcLys | L-N-Acetyllysine |
| Dpr | L-2,3-Diaminopropionic acid |
| A$_2$Bu | L-2,4-Diaminobutyric acid |
| Dbu | (S)-2,3-Diaminobutyric acid |
| Abu | γ-Aminobutyric acid (GABA) |
| Aha | ε-Aminohexanoic acid |
| Aib | α-Aminoisobutyric acid |
| Y(Bzl) | L-O-Benzyltyrosine |
| Bip | L-Biphenylalanine |
| S(Bzl) | L-O-Benzylserine |
| T(Bzl) | L-O-Benzylthreonine |
| hCha | L-Homo-cyclohexylalanine |
| hCys | L-Homo-cysteine |
| hSer | L-Homo-serine |
| hArg | L-Homo-arginine |
| hPhe | L-Homo-phenylalanine |
| Bpa | L-4-Benzoylphenylalanine |
| Pip | L-Pipecolic acid |
| OctG | L-Octylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methvaline |
| MeLeu | L-N-Methylleucine |
| BnG | N-Benzylglycine |
| (4-OH)BnG | N-4-Hydroxy-benzylglycine |
| IaG | N-Isoamylglycine |
| IbG | N-Isobutlyglycine |
| (EA)G | N-(2-Aminoethyl)glycine |
| (PrA)G | N-(3-Amino n-propyl)glycine |
| (BA)G | N-(4-Amino-n-butyl)glycine |
| (PeA)G | N-(5-Amino-n-pentyl)glycine |
| (EGU)G | N-(2-Guanidinoethyl)glycine |
| (PrGU)G | N-(3-Guanidino-n-propyl)glycine |
| (BGU)G | N-(4-Guanidino-n-butyl)glycine |
| (PeGU)G | N-(5-Guanidino-n-pentyl)glycine |
| (PEG$_3$-NH$_2$)G | N-[(CH$_2$)$_3$O—(CH$_2$—CH$_2$O)$_2$—(CH$_2$)$_3$—NH$_2$]glycine |
| (Et—CONH$_2$)G | N-(2-Carbamoylethyl)glycine |
| (Et—OH)G | N-(2-Hydroxyethyl)glycine |
| (CH$_2$—CONH$_2$)G | N-(Carbamoylmethyl)glycine |
| (n-Pr—NHCONH$_2$)G | N-(3-Ureyl-n-propyl)glycine |
| (Et—SH)G | N-(2-Mercaptoethyl)glycine |

In addition, the most preferred values for B also include groups of type A8" of (L)-configuration:

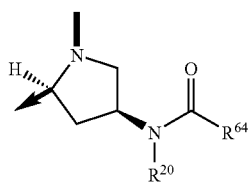

wherein $R^{20}$ is H or lower alkyl and $R^{64}$ is alkyl; alkenyl; aryl; aryl-lower alkyl; or heteroaryl-lower alkyl; especially those wherein $R^{64}$ is n-hexyl (A8"-21); n-heptyl (A8"-22); 4-(phenyl)benzyl (A8"-23); diphenylmethyl (A8"-24); 3-aminopropyl (A8"-25); 5-amino-pentyl (A8"-26); methyl (A8"-27); ethyl (A8"-28); isopropyl (A8"-29); isobutyl (A8"-30); n-propyl (A8"-31); cyclohexyl (A8"-32); cyclohexylmethyl (A8"-33); n-butyl (A8"-34); phenyl (A8"-35); benzyl (A8"-36); (3-indolyl)methyl (A8"-37); 2-(3-indolyl)ethyl (A8"-38); (4-phenyl)phenyl (A8"-39); and n-nonyl (A8"-40).

The peptidic chain Z of the β-hairpin mimetics described herein are generally defined in terms of amino acid residues belonging to one of the following groups:

| | | |
|---|---|---|
| Group C | —$NR^{20}CH(R^{72})CO$—; | "hydrophobic: small to medium-sized" |
| Group D | —$NR^{20}CH(R^{73})CO$—; | "hydrophobic: large aromatic or heteroaromatic" |
| Group E | —$NR^{20}CH(R^{74})CO$—; | "polar-cationic" and "urea-derived" |
| Group F | —$NR^{20}CH(R^{84})CO$—; | "polar-non-charged" |
| Group H | —$NR^{20}$—$CH(CO$—$)$—$(CH_2)_{4-7}$—$CH(CO$—$)$—$NR^{20}$—; | |
| | —$NR^{20}$—$CH(CO$—$)$—$(CH_2)_p SS(CH_2)_p$—$CH(CO$—$)$—$NR^{20}$—; | |
| | —$NR^{20}$—$CH(CO$—$)$—$(-(CH_2)_p NR^{20}CO(CH_2)_p$—$CH(CO$—$)$—$NR^{20}$—; and | |
| | —$NR^{20}$—$CH(CO$—$)$—$(-(CH_2)_p NR^{20}CONR^{20}(CH_2)_p$—$CH(CO$—$)$—$NR^{20}$—; | |
| | "interstrand linkage" | |
| Group I | —$NR^{86}CH_2CO$—; | "polar-cationic" |
| Group K | —$NR^{87}CH_2CO$—; | "polar non charged" |

Furthermore, the amino acid residues in chain Z can also be of formula -A-CO— or of formula —B—CO— wherein A and B are as defined above. Finally Pro can be an amino acid residue in chain Z, too, with the exception of positions where interstrand linkages (H) are possible.

Group C comprises amino acid residues with small to medium-sized hydrophobic side chain groups according to the general definition for substituent $R^{72}$. A hydrophobic residue refers to an amino acid side chain that is uncharged at physiological pH and that is repelled by aqueous solution. Furthermore these side chains generally do not contain hydrogen bond donor groups, such as (but not limited to) primary and secondary amides, primary and secondary amines and the corresponding protonated salts thereof, thiols, alcohols, phosphonates, phosphates, ureas or thioureas. However, they may contain hydrogen bond acceptor groups such as ethers, thioethers, esters, tertiary amides, alkyl- or aryl phosphonates and phosphates or tertiary amines. Genetically encoded small-to-medium-sized amino acids include alanine, isoleucine, leucine, methionine and valine.

Group D comprises amino acid residues with aromatic and heteroaromatic side chain groups according to the general definition for substituent $R^{73}$. An aromatic amino acid residue refers to a hydrophobic amino acid having a side chain containing at least one ring having a conjugated π-electron system (aromatic group). In addition they may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tetriary amides, alkyl- or aryl phosphonates—and phosphates or tertiary amines. Genetically encoded aromatic amino acids include phenylalanine and tyrosine.

A heteroaromatic amino acid residue refers to a hydrophobic amino acid having a side chain containing at least one ring having a conjugated π-system incorporating at least one heteroatom such as (but not limited to) O, S and N according to the general definition for substituent $R^{77}$. In addition such residues may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tertiary amides, alkyl- or aryl phosphonates—and phosphates or tertiary amines. Genetically encoded heteroaromatic amino acids include tryptophan and histidine.

Group E comprises amino acids containing side chains with polar-cationic, acylamnino- and urea-derived residues according to the general definition for substituent $R^{74}$. Polar-cationic refers to a basic side chain which is protonated at physiological pH. Genetically encoded polar-cationic amino acids include arginine, lysine and histidine. Citrulline is an example for an urea derived amino acid residue.

Group F comprises amino acids containing side chains with polar-non-charged residues according to the general definition for substituent $R^{84}$. A polar-non-charged residue refers to a hydrophilic side chain that is uncharged at physiological pH, but that is not repelled by aqueous solutions. Such side chains typically contain hydrogen bond donor groups such as (but not limited to) primary and secondary amides, primary and secondary amines, thiols, alcohols, phosphonates, phosphates, ureas or thioureas. These groups can form hydrogen bond networks with water molecules. In addition they may also contain hydrogen bond acceptor groups such as (but not limited to) ethers, thioethers, esters, tetriary amides, alkyl- or aryl phosphonates—and phosphates or tertiary amines. Genetically encoded polar-non-charged amino acids include asparagine, cysteine, glutamine, serine and threonine.

Group H comprises side chains of preferably (L)-amino acids at opposite positions of the β-strand region that can form an interstrand linkage. The most widely known linkage is the disulfide bridge formed by cysteines and homo-cysteines positioned at opposite positions of the β-strand. Various methods are known to form disulfide linkages including those described by: J. P. Tam et al. *Synthesis* 1979, 955-957; Stewart et al., *Solid Phase Peptide Synthesis,* 2d Ed., Pierce Chemical Company, Ill., 1984; Ahmed et al. J. Biol. Chem. 1975, 250, 8477-8482; and Pennington et al., *Peptides*, pages 164-166, Giralt and Andreu, Eds., ESCOM Leiden, The Netherlands, 1990. Most advantageously, for the scope of the present invention, disulfide linkages can be prepared using acetamidomethyl (Acm)-protective groups for cysteine. A well established interstrand linkage consists in linking ornithines and lysines, respectively, with glutamic and aspartic acid residues located at opposite β-strand positions by means of an amide bond formation. Preferred protective groups for the side chain amino-groups of ornithine and lysine are allyloxycarbonyl (Alloc) and allylesters for aspartic and glutamic acid. Finally, interstrand linkages can also be established by linking the amino groups of lysine and ornithine located at opposite β-strand positions with reagents such as N,N-carbonylimidazole to form cyclic ureas.

Group I comprises glycine having the amino group substituted by chains containing polar-cationic residues according to the general definition for substituent $R^{86}$. Polar-cationic refers to a basic side chain which is protonated at physiological pH.

Group K comprises glycine having the amino group substituted by chains containing polar-non-charged residues according to the general definition for substituent $R^{87}$. A polar-non-charged residue refers to a hydrophilic side chain that is uncharged at physiological pH, but that is not repelled by aqueous solutions. Such side chains typically contain hydrogen bond donor groups such as (but not limited to) primary and secondary amides, thiols, alcohols, or ureas. These groups can form hydrogen bond networks with water molecules. In addition they may also contain hydrogen bond acceptor groups such as (but not limited to) ether, thioether, ester or tertiary amino groups.

As mentioned earlier, positions for interstrand linkages are positions P4 and P9 and/or P2 and P11 taken together.

Such interstrand linkages are known to stabilize the β-hairpin conformations and thus constitute an important structural element for the design of β-hairpin mimetics.

Preferred amino acid residues (other than of types I and K) in chain Z are those derived from natural α-amino acids. Hereinafter follows a list of amino acids which, or the residues of which, are suitable for the purposes of the present invention, the abbreviations corresponding to generally adopted usual practice:

| three letter code | | one letter code |
|---|---|---|
| Ala | L-Alanine | A |
| Arg | L-Arginine | R |
| Asn | L-Asparagine | N |
| Asp | L-Aspartic acid | D |
| Cys | L-Cysteine | C |
| Glu | L-Glutamic acid | E |
| Gln | L-Glutamine | Q |
| Gly | Glycine | G |
| His | L-Histidine | H |
| Ile | L-Isoleucine | I |
| Leu | L-Leucine | L |
| Lys | L-Lysine | K |
| Met | L-Methionine | M |
| Phe | L-Phenylalanine | F |
| Pro | L-Proline | P |
| $^D$Pro | D-Proline | $^D$P |
| Ser | L-Serine | S |

-continued

| three letter code | | one letter code |
|---|---|---|
| Thr | L-Threonine | T |
| Trp | L-Tryptophan | W |
| Tyr | L-Tyrosine | Y |
| Val | L-Valine | V |

Other α-amino acids which, or the residues of which, are suitable for the purposes of the present invention include:

| | |
|---|---|
| Cit | L-Citrulline |
| Orn | L-Ornithine |
| tBuA | L-t-Butylalanine |
| Sar | Sarcosine |
| Pen | L-Penicillamine |
| t-BuG | L-tert.-Butylglycine |
| 4AmPhe | L-para-Aminophenylalanine |
| 3AmPhe | L-meta-Aminophenylalanine |
| 2AmPhe | L-ortho-Aminophenylalanine |
| Phe(mC(NH$_2$)=NH) | L-meta-Amidinophenylalanine |
| Phe(pC(NH$_2$)=NH) | L-para-Amidinophenylalanine |
| Phe(mNHC(NH$_2$)=NH) | L-meta-Guanidinophenylalanine |
| Phe(pNHC(NH$_2$)=NH) | L-para-Guanidinophenylalanine |
| Phg | L-Phenylglycine |
| Cha | L-Cyclohexylalanine |
| C$_4$al | L-3-Cyclobutylalanine |
| C$_5$al | L-3-Cyclopentylalanine |
| Nle | L-Norleucine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4Cl$_2$-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Tic | 1,2,3,4-Tetrahydroisoquinoline-3-carboxylic acid |
| Thi | L-β-2-Thienylalanine |
| Tza | L-2-Thiazolylalanine |
| Mso | L-Methionine sulfoxide |
| AcLys | N-Acetyllysine |
| Dpr | 2,3-Diaminopropionic acid |
| A$_2$Bu | 2,4-Diaminobutyric acid |
| Dbu | (S)-2,3-Diaminobutyric acid |
| Abu | γ-Aminobutyric acid (GABA) |
| Aha | ε-Aminohexanoic acid |
| Aib | α-Aminoisobutyric acid |
| Y(Bzl) | L-O-Benzyltyrosine |
| Bip | L-(4-phenyl)phenylalanine |
| S(Bzl) | L-O-Benzylserine |
| T(Bzl) | L-O-Benzylthreonine |
| hCha | L-Homo-cyclohexylalanine |
| hCys | L-Homo-cysteine |
| hSer | L-Homo-serine |
| hArg | L-Homo-arginine |
| hPhe | L-Homo-phenylalanine |
| Bpa | L-4-Benzoylphenylalanine |
| 4-AmPyrr1 | (2S,4S)-4-Amino-pyrrolidine-L-carboxylic acid |
| 4-AmPyrr2 | (2S,4R)-4-Amino-pyrrolidine-L-carboxylic acid |
| 4-PhePyrr1 | (2S,5R)-4-Phenyl-pyrrolidine-L-carboxylic acid |
| 4-PhePyrr2 | (2S,5S)-4-Phenyl-pyrrolidine-L-carboxylic acid |
| 5-PhePyrr1 | (2S,5R)-5-Phenyl-pyrrolidine-L-carboxylic acid |
| 5-PhePyrr2 | (2S,5S)-5-Phenyl-pyrrolidine-L-carboxylic acid |
| Pro(4-OH)1 | (4S)-L-Hydroxyproline |
| Pro(4-OH)2 | (4R)-L-Hydroxyproline |
| Pip | L-Pipecolic acid |
| $^D$Pip | D-Pipecolic acid |
| OctG | L-Octylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methylvaline |

-continued

| | |
|---|---|
| MeLeu | L-N-Methylleucine |
| BnG | N-Benzylglycine |
| (4-OH)BnG | N-4-Hydroxy-benzylglycine |
| IaG | N-Isoamylglycine |
| IbG | N-Isobutlyglycine |
| (EA)G | N-(2-Aminoethyl)glycine |
| (PrA)G | N-(3-Amino-n-propyl)glycine |
| (BA)G | N-(4-Amino-n-butyl)glycine |
| (PeA)G | N-(5-Amino-n-pentyl)glycine |
| (EGU)G | N-(2-Guanidinoethyl)glycine |
| (PrGU)G | N-(3-Guanidino-n-propyl)glycine |
| (BGU)G | N-(4-Guanidino-n-butyl)glycine |
| (PeGU)G | N-(5-Guanidino-n-pentyl)glycine |
| (PEG$_3$-NH$_2$)G | N-[(CH$_2$)$_3$O—(CH$_2$—CH$_2$O)$_2$—(CH$_2$)$_3$—NH$_2$]glycine |
| (Et—CONH$_2$)G | N-(2-Carbamoylethyl)glycine |
| (Et—OH)G | N-(2-Hydroxyethyl)glycine |
| (CH$_2$—CONH$_2$)G | N-(Carbamoylmethyl)glycine |
| (n-Pr—NHCONH$_2$)G | N-(3-Ureyl-n-propyl)glycine |
| (Et—SH)G | N-(2-Mercaptoethyl)glycine |

Particularly preferred residues for group C are

| | |
|---|---|
| Ala | L-Alanine |
| Ile | L-Isoleucine |
| Leu | L-Leucine |
| Met | L-Methionine |
| Val | L-Valine |
| tBuA | L-t-Butylalanine |
| t-BuG | L-tert.-Butylglycine |
| Cha | L-Cyclohexylalanine |
| C$_4$al | L-3-Cyclobutylalanine |
| C$_5$al | L-3-Cyclopentylalanine |
| Nle | L-Norleucine |
| hCha | L-Homo-cyclohexylalanine |
| OctG | L-Octylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methylvaline |
| MeLeu | L-N-Methylleucine |
| BnG | N-Benzylglycine |
| (4-OH)BnG | N-4-Hydroxy-benzylglycine |
| IaG | N-Isoamylglycine |
| IbG | N-Isobutlyglycine |

Particularly preferred residues for group D are

| | |
|---|---|
| His | L-Histidine |
| Phe | L-Phenylalanine |
| Trp | L-Tryptophan |
| Tyr | L-Tyrosine |
| Phg | L-Phenylglycine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4Cl$_2$-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Thi | L-β-2-Thienylalanine |
| Tza | L-2-Thiazolylalanine |
| Y(Bzl) | L-O-Benzyltyrosine |
| Bip | L-Biphenylalanine |
| S(Bzl) | L-O-Benzylserine |
| T(Bzl) | L-O-Benzylthreonine |
| hPhe | L-Homo-phenylalanine |
| Bpa | L-4-Benzoylphenylalanine |

Particularly preferred residues for group E are

| | |
|---|---|
| Arg | L-Arginine |
| Lys | L-Lysine |
| Orn | L-Ornithine |
| Dpr | L-2,3-Diaminopropionic acid |
| A$_2$Bu | L-2,4-Diaminobutyric acid |
| Dbu | (S)-2,3-Diaminobutyric acid |
| Phe(pNH$_2$) | L-para-Aminophenylalanine |
| Phe(mNH$_2$) | L-meta-Aminophenylalanine |
| Phe(oNH$_2$) | L-ortho-Aminophenylalanine |
| hArg | L-Homo-arginine |
| Phe(mC(NH$_2$)=NH) | L-meta-Amidinophenylalanine |
| Phe(pC(NH$_2$)=NH) | L-para-Amidinophenylalanine |
| Phe(mNHC (NH$_2$)=NH) | L-meta-Guanidinophenylalanine |
| Phe(pNHC (NH$_2$)=NH) | L-para-Guanidinophenylalanine |
| Cit | L-Citrulline |

Particularly preferred residues for group F are

| | |
|---|---|
| Asn | L-Asparagine |
| Cys | L-Cysteine |
| Gln | L-Glutamine |
| Ser | L-Serine |
| Thr | L-Threonine |
| Cit | L-Citrulline |
| Pen | L-Penicillamine |
| AcLys | L-N$^ε$-Acetyllysine |
| hCys | L-Homo-cysteine |
| hSer | L-Homo-serine |

Particularly preferred residues for group I are

| | |
|---|---|
| (EA)G | N-(2-Aminoethyl)glycine |
| (PrA)G | N-(3-Amino-n-propyl)glycine |
| (BA)G | N-(4-Amino-n-butyl)glycine |
| (PeA)G | N-(5-Amino-n-pentyl)glycine |
| (EGU)G | N-(2-Guanidinoethyl)glycine |
| (PrGU)G | N-(3-Guanidino-n-propyl)glycine |
| (BGU)G | N-(4-Guanidino-n-butyl)glycine |
| (PeGU)G | N-(5-Guanidino-n-pentyl)glycine |
| (PEG$_3$-NH$_2$)G | N-[(CH$_2$)$_3$O—(CH$_2$—CH$_2$O)$_2$—(CH$_2$)$_3$—NH$_2$]glycine |

Particularly preferred residues for group K are

| | |
|---|---|
| (Et—CONH$_2$)G | N-(2-Carbamoylethyl)glycine |
| (CH$_2$—CONH$_2$)G | N-(Carbamoylmethyl)glycine |
| (n-Pr—NHCONH$_2$)G | N-(3-Ureyl-n-propyl)glycine |
| (Et—SH)G | N-(2-Mercaptoethyl)glycine |
| (Et—OH)G | N-(2-Hydroxyethyl)glycine |

Generally, the peptidic chain Z within the β-hairpin mimetics of the invention comprises 12 amino acid residues. The positions P1 to P12 of each amino acid residue in the chain Z are unequivocally defined as follows: P1 represents the first amino acid in the chain Z that is coupled with its N-terminus to the C-terminus of the templates (b)-(p) or of group —B—CO— in template (a1), or of group -A-CO— in template (a2), and P12 represents the last amino acid in the chain Z that is coupled with its C-terminus to the N-terminus of the templates (b)-(p) or of group -A-CO— in template (a1) or of group —B—CO— in template (a2). Each of the positions P1 to P12 will preferably contain an amino acid residue belonging to one of the above types C, D, E, F or I, or of formula —A1-A69-CO— or of formula —B—CO—, as follows:
P1: of type C or of type D or of type E or of type F;
P2: of type D or of type E;
P3: of type C;
P4: of type E or of type I or of type F;
P5: of type E or of type I or of type F;
P6: of type E or of type I or of type D or of formula —A1-A69-CO;
P7: of type E or of type I or of type C or of formula B—CO;
P8: of type D;
P9: of type E;
P10: of type D or of type C;
P11: of type E or of type D; or of type C and
P12: of type C or of type D or of type E or of type F;
at P6 and P7 also D-isomers being possible;
with the proviso that at least one of the amino acid residues is of type I.

Most preferably the amino acid residues in position 1-12 are:
P1: Leu; Thr; or Arg;
P2: Arg; or Trp;
P3: Leu;
P4: Lys; hArg; (BA)G; or Gln;
P5: Lys; Gln; hArg; or (PeA)G;
P6: Arg, Trp, hArg; (EGU)G;
    (EA)G; (PrA)G; (PeA)G or (BA)G;
P7: Arg; (PeA)G; or Val
P8: Trp; or Bip;
P9: Lys; Arg; or hArg;
P10: Tyr;
P11: Arg; or Tyr; and
P12: Val; or Arg;
with the proviso that
the amino acid residue in P4 is (BA)G; and/or
the amino acid residue in P5 is (PeA)G; and/or
the amino acid residue in P6 is (EGU)G or
    (EA)G or (PRA)G or (PEA)G or (BA)G; and/or
the amino acid residue in P7 is (PeA)G.

Particularly preferred β-peptidomimetics of the invention include those described in examples 1 to 12.

The process of the invention can advantageously be carried out as parallel array synthesis to yield libraries of template-fixed β-hairpin peptidomimetics of the above general formula I. Such parallel synthesis allows one to obtain arrays of numerous (normally 24 to 192, typically 96) compounds of general formula I in high yields and defined purities, minimizing the formation of dimeric and polymeric by-products. The proper choice of the functionalized solid-support (i.e. solid support plus linker molecule), templates and site of cyclization play thereby key roles.

The functionalized solid support is conveniently derived from polystyrene cross linked with, preferably 1-5%, divinylbenzene; polystyrene coated with polyethyleneglycol spacers (Tentagel®); and polyacrylamide resins (see also Obrecht, D.; Villalgordo, J.-M, "Solid-Supported Combinatorial and Parallel Synthesis of Small-Molecular-Weight Compound Libraries", Tetrahedron Organic Chemistry Series, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention the linker must be designed to eventually release the carboxyl group under mild acidic conditions which do not affect protecting groups present on any functional group in the side-chains of the various amino acids. Linkers which are suitable for the purposes of the present invention form acid-labile esters with the carboxyl group of the amino acids, usually acid-labile benzyl, benzhydryl and trityl esters; examples of linker structures of this kind include 2-methoxy-4-hydroxymethylphenoxy (Sasrin® linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl.

Preferably, the support is derived from polystyrene crosslinked with, most preferably 1-5%, divinylbenzene and functionalized by means of the 2-chlorotrityl linker.

When carried out as a parallel array synthesis the process of the invention can be advantageously carried out as described herein below but it will be immediately apparent to those skilled in the art how this procedure will have to be modified in case it is desired to synthesize one single compound of the above formula I.

A number of reaction vessels (normally 24 to 192, typically 96) equal to the total number of compounds to be synthesized by the parallel method are loaded with 25 to 1000 mg, preferably 100 mg, of the appropriate functionalized solid support, preferably 1 to 3% cross linked polystyrene or tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (Fields, G. B., Fields, C. G., *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin® linker, Mergler et al., *Tetrahedron Lett.* 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the process of the invention include the super acid labile 4-(2,4-dimethoxyphenyl-hydroxymethyl)-phenoxy linker (Rink linker, Rink, H. *Tetrahedron Lett.* 1987, 28, 3787-3790), where the removal of the peptide requires 10% acetic acid in DCM or 0.2% trifluoroacetic acid in DCM; the 4-(4-hydroxymethyl-3-methoxyphenoxy)butyric acid-derived linker (HMPB-tinker, Flörsheimer & Riniker, *Peptides* 1991, 1990 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943-3946), which allows the peptide detachment using a mixture of glacial acetic acid/trifluoroethanol/DCM (1:2:7) for 30 min.

Suitable protecting groups for amino acids and, respectively, for their residues are, for example, for the amino group (as is present e. g. also in the side-chain of lysine)

| | |
|---|---|
| Cbz | benzyloxycarbonyl |
| Boc | tert.-butyloxycarbonyl |
| Fmoc | 9-fluorenylmethoxycarbonyl |
| Alloc | allyloxycarbonyl |
| Teoc | trimethylsilylethoxycarbonyl |
| Tcc | trichloroethoxycarbonyl |
| Nps | o-nitrophenylsulfonyl; |
| Trt | triphenymethyl or trityl | for the carboxyl group (as is present e. g. also in the side-chain of aspartic and glutamic acid) by conversion into esters with the alcohol components

| | |
|---|---|
| tBu | tert.-butyl |
| Bn | benzyl |
| Me | methyl |
| Ph | phenyl |
| Pac | Phenacyl |
| | Allyl |
| Tse | trimethylsilylethyl |
| Tce | trichloroethyl; | for the guanidino group (as is present e. g. in the side-chain of arginine)

| | |
|---|---|
| Pmc | 2,2,5,7,8-pentamethylchroman-6-sulfonyl |
| Ts | tosyl (i.e. p-toluenesulfonyl) |
| Cbz | benzyloxycarbonyl |
| Pbf | pentamethyldihydrobenzofuran-5-sulfonyl | for the hydroxy group (as is present e. g. in the side-chain of threonine and serine)

| | |
|---|---|
| tBu | tert.-butyl |
| Bn | benzyl |
| Trt | trityl | and for the mercapto group (as is present e. g. in the side-chain of cysteine)

| | |
|---|---|
| Acm | acetamidomethyl |
| tBu | tert.-butyl |
| Bn | benzyl |
| Trt | trityl |
| Mtr | 4-methoxytrityl. |

The 9-fluorenylmethoxycarbonyl-(Fmoc)-protected amino acid derivatives are preferably used as the building blocks for the construction of the template-fixed β-hairpin loop mimetics of formula I. For the deprotection, i. e. cleaving off of the Fmoc group, 20% piperidine in DMF or 2% DBU/ 2% piperidine in DMF can be used.

The N-substituted glycine derivatives (types I and K) used as building blocks for the construction of the template-fixed β-hairpin loop mimetics of formula I are derived from 9-fluorenylmethoxycarbonyl-(Fmoc)-protected amino acid derivatives or preferably built up in two steps from leaving group-containing glycine precursors, such as bromo, chloro or iodo acetic acid, and suitable primary amine building blocks $NH_2$—$R^{86}$ or $NH_2$—$R^{87}$ according to definition of $R^{86}$ or $R^{87}$. The first synthesis step consists of the attachment of the leaving group-containing acetylating agent, such as bromo acetic acid, to the resin bound intermediate through formation of the amide bond. The second reaction step—the nucleophilic displacement—is accomplished using the primary amine building blocks, wherein the residues are, if necessary, suitably protected with groups as described above for side chains of amino acids.

For the incorporation of the N-substituted glycine derivatives as building blocks into the template-fixed β-hairpin loop mimetics the general synthesis procedure for assembling the hairpin mimetics is used as described herein.

The quantity of the reactant, i. e. of the amino acid derivative or leaving group-containing glycine precursor, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used if required to drive the reaction to completion in a reasonable time. The reaction tubes, in combination with the holder block and the manifold, are reinserted into the reservoir block and the apparatus is fastened together. Gas flow through the manifold is initiated to provide a controlled environment, for example, nitrogen, argon, air and the like. The gas flow may also be heated or chilled prior to flow through the manifold. Heating or cooling of the reaction wells is achieved by heating the reaction block or cooling externally with isopropanol/dry ice and the like to bring about the desired synthetic reactions. Agitation is achieved by shaking or magnetic stirring (within the reaction tube). The preferred workstations (without, however, being limited thereto) are Labsource's Combi-chem station, ABI 433A and MultiSyn Tech's-Syro synthesizer.

Amide bond formation requires the activation of the α-carboxyl group for the acylation step. When this activation is being carried out by means of the commonly used carbodiimides such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea is insoluble and, respectively, diisopropylurea is soluble in the solvents generally used. In a variation of the carbodiimide method 1-hydroxybenzotriazole (HOBt, König & Geiger, *Chem. Ber* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethylamino)-phosphonium hexafluorophosphate (BOP) (Castro et al., *Tetrahedron Lett.* 1975, 14, 1219-1222; *Synthesis,* 1976, 751-752), or benzotriazol-1-yl-oxy-tris-pyrrolidino-phosphonium hexaflurophoshate (Py-BOP, Coste et al., *Tetrahedron Lett.* 1990, 31, 205-208), or 2-(1H-benzotriazol-1-yl-)1,1,3,3-tetramethyluronium terafluoroborate (TBTU), or hexafluorophosphate (HBTU, Knorr et al., *Tetrahedron Lett.* 1989, 30, 1927-1930); these phosphonium reagents are also suitable for in situ formation of HOBt esters with the protected amino acid derivatives. More recently diphenoxyphosphoryl azide (DPPA) or O-(7-aza-benzotriazol-1-yl)-N,N,N', N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzotriazole (HOAt, Carpino et al., *Tetrahedron Lett.* 1994, 35, 2279-2281) have also been used as coupling reagents.

Due to the fact that near-quantitative coupling reactions are essential it is desirable to have experimental evidence for completion of the reactions. The ninhydrin test (Kaiser et al., *Anal. Biochemistry* 1970, 34, 595), where a positive colorimetric response to an aliquot of resin-bound peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35-42).

The nucleophilic displacement reaction substituting the leaving group of the glycine precursor is preferably performed in DMF. The typical amount of the primary amine building block used for the nucleophilic displacement reaction is between 1 and 12 eq based on the milliequivalents per gram (meq/g) loading of the functionalized solid support. The experimental evidence for completion of the acetylation- and the following nucleophilic displacement reaction of the two-step procedure for assembling N-substituted glycine derivatives used as building blocks is usually not monitored (R. N. Zuckermann, *J. Am. Chem. Soc.* 1992, 114, 10646-10647 and cited references).

The resin-bound intermediate within each reaction tube is washed free of excess of retained reagents, of solvents, and of by-products by repetitive exposure to pure solvent(s) by one of the two following methods:

1) The reaction wells are filled with solvent (preferably 5 ml), the reaction tubes, in combination with the holder block and manifold, are immersed and agitated for 5 to 300 minutes, preferably 15 minutes, and drained by gravity followed by gas pressure applied through the manifold inlet (while closing the outlet) to expel the solvent;

2) The manifold is removed from the holder block, aliquots of solvent (preferably 5 ml) are dispensed through the top of the reaction tubes and drained by gravity through a filter into a receiving vessel such as a test tube or vial.

Both of the above washing procedures are repeated up to about 50 times (preferably about 10 times), monitoring the efficiency of reagent, solvent, and byproduct removal by methods such as TLC, GC, or inspection of the washings.

The above described procedure of reacting the resin-bound compound with reagents within the reaction wells followed by removal of excess reagents, by-products, and solvents is repeated with each successive transformation until the final resin-bound fully protected linear peptide has been obtained.

Before this fully protected linear peptide is detached from the solid support, it is possible, if desired, to selectively deprotect one or several protected functional group(s) present in the molecule and to appropriately substitute the reactive group(s) thus liberated. To this effect, the functional group(s) in question must initially be protected by a protecting group which can be selectively removed without affecting the remaining protecting groups present. Alloc (allyloxycarbonyl) is an example for such a protecting group for amino which can be selectively removed, e.g. by means of $Pd^\circ$ and phenylsilane in $CH_2Cl_2$, without affecting the remaining protecting groups, such as Fmoc, present in the molecule. The reactive group thus liberated can then be treated with an agent suitable for introducing the desired substituent. Thus, for example, an amino group can be acylated by means of an acylating agent corresponding to the acyl substituent to be introduced.

Detachment of the fully protected linear peptide from the solid support is achieved by immersion of the reaction tubes, in combination with the holder block and manifold, in reaction wells containing a solution of the cleavage reagent (preferably 3 to 5 ml). Gas flow, temperature control, agitation, and reaction monitoring are implemented as described above and as desired to effect the detachment reaction. The reaction tubes, in combination with the holder block and manifold, are disassembled from the reservoir block and raised above the solution level but below the upper lip of the reaction wells, and gas pressure is applied through the manifold inlet (while closing the outlet) to efficiently expel the final product solution into the reservoir wells. The resin remaining in the reaction tubes is then washed 2 to 5 times as above with 3 to 5 ml of an appropriate solvent to extract (wash out) as much of the detached product as possible. The product solutions thus obtained are combined, taking care to avoid cross-mixing. The individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Cyclization is then effected in solution using solvents such as DCM, DMF, dioxane, THF and the like. Various coupling reagents which were mentioned earlier can be used for the cyclization. The duration of the cyclization is about 6-48 hours, preferably about 24 hours. The progress of the reaction is followed, e. g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Before removing the protecting groups from the fully protected cyclic peptide, it is possible, if desired, to form an interstrand linkage between side-chains of appropriate amino acid residues at opposite positions of the β-strand region.

Interstrand linkages and their formation have been discussed above, in connection with the explanations made regarding groups of the type H which can, for example, be disulfide bridges formed by cysteines and homocysteines at opposite positions of the β-strand, or glutamic and aspartic acid residues linking ornithines and, respectively, lysines located at opposite β-strand positions by amide bond formation. The formation of such interstrand linkages can be effected by methods well known in the art.

The fully protected peptide derivative of type I is treated with 95% TFA, 2.5% $H_2O$, 2.5% TIS or another combination of scavengers for effecting the cleavage of protecting groups. The cleavage reaction time is commonly 30 minutes to 12 hours, preferably about 2 hours.

After the deprotection it is possible, if desired, to convert any amino group(s) present in the molecule into guanidino groups using appropriate guanidinylation reagents (K. Feichinger et al, *J. Org. Chem.* 1998, 63, 3804-2805). Suitable guanidinylation reagents include, but are not limited to, N,N-di-Boc-trifluoromethanesulfonylguanidine. Such guanidinylation will convert, for example, any (EA)G residue to (EGU)G and, simultaneously, any Lys residue to hArg.

Finally thereafter most of the solvent (such as TFA) which usually still is present is evaporated and the product is precipitated with ether/hexane (1:1) or other solvents which are suitable therefor. After careful removal of the solvent, the cyclic peptide derivative obtained as end-product can be isolated. Depending on its purity, this peptide derivative can be used directly for biological assays, or it has to be further purified, for example by preparative HPLC.

As mentioned earlier, it is thereafter possible, if desired, to convert a compound of formula I thus obtained into a pharmaceutically acceptable salt or to convert a pharmaceutically acceptable, or unacceptable, salt thus obtained into the corresponding free compound of formula I or into a different, pharmaceutically acceptable, salt. Any of these operations can be carried out by methods well known in the art.

The template starting materials of formula II used in the processes of the invention, pre-starting materials therefor, and the preparation of these starting and pre-starting materials are described in International Application PCT/EP02/01711 of the same applicants, published as WO 02/070547 A1.

The starting materials of formulae $H_2NR^{86}$ and $H_2NR^{87}$ are known or can be prepared by methods which are well known in the art.

The β-hairpin peptidomimetics of the invention can be used in a wide range of applications in order to inhibit the growth of or to kill microorganisms.

They can be used for example as disinfectants or as preservatives for materials such as foodstuffs, cosmetics, medicaments and other nutrient-containing materials. The β-hairpin peptidomimetics of the invention can also be used to treat or prevent diseases related to microbial infection in plants and animals.

For use as disinfectants or preservatives the β-hairpin peptidomimetics can be added to the desired material singly, as mixtures of several β-hairpin peptidomimetics or in combination with other antimicrobial agents. The β-hairpin peptidomimetics may be administered per se or may be applied as an appropriate formulation together with carriers, diluents or excipients well known in the art.

When used to treat or prevent infections or diseases related to such infections particularly infections related to respiratory diseases such as cystic fibrosis, the β-hairpin peptidomimetics can be administered singly, as mixtures of several β-hairpin peptidomimetics, in combination with other antimicrobial or antibiotic agents or in combination with antiviral (e.g. anti-HIV) or anti cancer agents or in combination with other pharmaceutically active agents. The β-hairpin peptidomimetics can be administered per se or as pharmaceutical compositions.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxilliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hink's solution, Ringer's solution, or physiological saline buffer. The solution may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated by combining the active β-hairpin peptidomimetics of the invention with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion of a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, desintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the β-hairpin peptidomimetics of the invention are conveniently delivered in form of an aeorosol spray from pressurized packs or a nebulizer, with the use of a suitable propellant, e.g. dichlorodifluoromethane, trichlorofluromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as suppositories together with appropriate suppository bases such as cocoa butter or other glycerides.

In addition to the formulation described previously, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide also may be employed. Additionally, the β-hairpin peptidomimetics of the invention may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic agent, additional strategies for protein stabilization may be employed.

As the β-hairpin pepdidomimetics of the invention may contain charged residues, they may be included in any of the above-described formulations as free bases or as pharmaceutically acceptable salts. Pharmaceutically acceptable salts tend to be more soluble in aqueous and other protic solvents than are the corresponding free base forms.

The β-hairpin peptidomimetics of the invention, or compositions thereof, will generally be used in an amount effective to achieve the intended purpose. It is to be understood that the amount used will depend on a particular application.

For example, for use as a disinfectant or preservative, an antimicrobially effective amount of a β-hairpin peptidomimetic of the invention, or a composition thereof, is applied or added to the material to be disinfected or preserved. By antimicrobially effective amount is meant an amount of a β-hairpin peptidomimetic of the invention or composition that inhibits the growth of, or is lethal to, a target microbe population. While the antimicrobially effective amount will depend on a particular application, for use as disinfectants or preservatives the β-hairpin peptidomimetics of the invention, or compositions thereof, are usually added or applied to the material to be disinfected or preserved in relatively low amounts. Typically, the β-hairpin peptidomimetics of the invention comprise less than about 5% by weight of a disinfectant solution or material to be preserved, preferably less than 1% by weight and more preferably less than 0.1% by weight. An ordinary skilled expert will be able to determine antimicrobially effective amounts of particular β-hairpin peptidomimetics of the invention for particular applications without undue experimentation using, for example, the in vitro assays provided in the examples.

For use to treat or prevent microbial infections or diseases related to such infections, the β-hairpin peptidomimetics of the invention, or compositions thereof, are administered or applied in a therapeutically effective amount. By therapeutically effective amount is meant an amount effective in ameliorating the symptoms of, or ameliorate, treat or prevent microbial infections or diseases related thereto. Determination of a therapeutically effective amount is well within the capacities of those skilled in the art, especially in view of the detailed disclosure provided herein.

As in the case of disinfectants and preservatives, for topical administration to treat or prevent bacterial infections a therapeutically effective dose can be determined using, for example, the in vitro assays provided in the examples. The treatment may be applied while the infection is visible, or even when it is not visible. An ordinary skilled expert will be able to determine therapeutically effective amounts to treat topical infections without undue experimentation.

For systemic administration, a therapeutically effective dose can be estimated initially from in vitro assays. For example, a dose can be formulated in animal models to achieve a circulating β-hairpin peptidomimetic concentration range that includes the $IC_{50}$ as determined in the cell culture (i.e. the concentration of a test compound that is lethal to 50% of a cell culture), the MIC, as determined in cell culture (i.e. the concentration of a test compound that is lethal to 100% of a cell culture). Such information can be used to more accurately determine useful doses in humans.

Initial dosages can also be determined from in vivo data, e.g. animal models, using techniques that are well known in the art. One having ordinary skills in the art could readily optimize administration to humans based on animal data.

Dosage amounts for applications as antimicrobial agents may be adjusted individually to provide plasma levels of the β-hairpin peptidomimetics of the invention which are sufficient to maintain the therapeutic effect. Therapeutically effective serum levels may be achieved by administering multiple doses each day.

In cases of local administration or selective uptake, the effective local concentration of the β-hairpin peptidomimetics of the invention may not be related to plasma concentration. One having the skills in the art will be able to optimize therapeutically effective local dosages without undue experimentation.

The amount of β-hairpin peptidomimetics administered will, of course, be dependent on the subject being treated, on the subject's weight, the severity of the affliction, the manner of administration and the judgement of the prescribing physician.

The antimicrobial therapy may be repeated intermittently while infections are detectable or even when they are not detectable. The therapy may be provided alone or in combination with other drugs, such as for example antibiotics or other antimicrobial agents.

Normally, a therapeutically effective dose of the β-hairpin peptidomimetics described herein will provide therapeutic benefit without causing substantial toxicity.

Hemolysis of red blood cells is often employed for assessment of toxicity of related compounds such as protegrin or tachyplesin. Values are given as %-lysis of red blood cells observed at a concentration of 100 μg/ml. Typical values determined for cationic peptides such as protegrin and tachyplesin range between 30-40% with average MIC-values of 1-5 μg/ml over a wide range of pathogens. Normally, β-hairpin peptidomimetics of the invention will show hemolysis in a range of 0.5-10%, often in a range of 1-5%, at activity levels comparable to those mentioned above for protegrin and tachyplesin. Thus preferred compounds exhibit low MIC-values and low %-hemolysis of red blood cells observed at a concentration of 100 μg/ml.

Toxicity of the β-hairpin peptidomimetics of the invention herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans. The dosage of the β-hairpin peptidomimetics of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. Fingl et al. 1975, In: *The Pharmacological Basis of Therapeutics*, Ch. 1, p. 1).

The following Examples illustrate the invention in more detail but are not intended to limit its scope in any way. The following abbreviations are used in these Examples:

HBTU: 1-benzotriazol-1-yl-tetramethylurounium hexafluorophosphate (Knorr et al. *Tetrahedron Lett.* 1989, 30, 1927-1930)

HOBt: 1-hydroxybenzotriazole

DIEA: diisopropylethylamine

HOAT: 7-aza-1-hydroxybenzotriazole

HATU: O-(7-aza-benzotriazole-1-yl)-N,N,N',N'-tetramethyluronoium hexafluorophosphate Carpino et al. *Tetrahedron Lett.* 1994, 35, 2279-2281)

EXAMPLES

1. Peptide Synthesis

Coupling of the First Amino Acid Residue 1.0 g of 2-chlorotritylchloride resin (Barlos et al. *Tetrahedron Lett.* 1989, 30, 3943-3946) (1.08 mMol/g, 1.08 mmol) was filled into a dried flask. The resin was suspended in $CH_2Cl_2$ (10 ml) and allowed to swell at room temperature under constant stirring. The resin was treated two times with 0.18 g (1.2 eq) bromo acid acid and 0.738 ml (4 eq) of diisopropylethylamine (DIEA) in $CH_2Cl_2$ (10 ml), the mixture was shaken at 25° C. for 2 h. The resin was washed extensively ($CH_2Cl_2$/MeOH/DIEA: 17/2/1; $CH_2Cl_2$, DMF; $CH_2Cl_2$; $Et_2O$, 3 times each).

This was followed by nucleophilic substitution of bromine with a Boc-protected amine. Boc-protected amines used were Boc-NH—$CH_2$—$CH_2$—$NH_2$, Boc-NH—$CH_2$—$CH_2$—$CH_2$—$NH_2$ and Boc-NH—$CH_2$—$CH_2$—$CH_2$—$CH_2$—$NH_2$. The Boc-protected amine, dissolved (3 eq) in DMSO: $CH_2Cl_2$ 1:1 v/v 5 ml was added to the resin. The resin was washed with $CH_2Cl_2$, DMF, $CH_2Cl_2$ 5 ml, 3 times).

The resin was dried overnight.

The following preloaded resins were prepared: (EA)G-O-chlorotritylresin; (BA)G-O-chlorotritylresin; (PrA)G-O-chlorotritylresin.

Synthesis Cycle

The synthesis was carried out using a Syro-peptide synthesizer (Multisyntech) or an ABI 433A using 24 to 96 reaction vessels. In each vessel was placed 60 mg weight of the resin before loading) of the above resin. The following reaction cycles were programmed and carried out:

| Step | Reagent | Time |
|---|---|---|
| 1 | $CH_2Cl_2$, wash and swell (manual) | 3 × 1 min. |
| 2 | DMF, wash and swell | 1 × 5 min |
| 3 | 40% piperidine/DMF | 1 × 5 min. |
| 4 | DMF, wash | 5 × 2 min. |
| 5a | 5 equiv. Fmoc amino acid/DMF +5 eq. HBTU +5 eq. HOBt +5 eq. DIEA | 1 × 120 min. |
| 6 | DMF, wash | 4 × 2 min. |
| 7 | $CH_2Cl_2$, wash (at the end of the synthesis) | 3 × 2 min. |

Steps 3 to 6 are repeated to add each amino-acid or N-substituted glycine building block.

To introduce a N-substituted glycine building blocks into specific positions within the chain, the following steps 5b.1-5b.3 were used instead of step 5a.

5b.1: 11 equiv. $BrCH_2COOH$/DMF+13 equiv. DIC, 90 min;

5b.2: DMF, wash 4×2 min;

5b.3: 20 equiv. amine building block with protected residue/DMF, 120 min.

Moreover, if a N-substituted glycine building block had been introduced in the previous cycle, step 5a was modified as follows: HBTU and HOBt were replaced by 3.5 eq. HATU, and 7 eq DIEA were used.

Cleavage of the Fully Protected Peptide Fragment

After completion of the synthesis, the resin was suspended in 1 ml (0.39 mMol) of 1% TFA in $CH_2Cl_2$ (v/v) for 3 minutes, filtered and the filtrate was neutralized with 1 ml (1.17 mMol, 3 eq.) of 20% DIEA in $CH_2Cl_2$ (v/v). This procedure was repeated twice to ensure completion of the cleavage. The filtrate was evaporated to dryness and a sample of the product was fully deprotected to be analyzed by reverse phase-HPLC (column $C_{18}$) to monitor the efficiency of the linear peptide synthesis.

Cyclization of the Linear Peptide 100 mg of the fully protected linear peptide were dissolved in DMF (9 ml, conc. 10 mg/ml). Then 41.8 mg (0.110 mMol, 3 eq.) of HATU, 14.9 mg (0.110 mMol, 3 eq) of HOAt and 1 ml (0.584 mMol) of 10% DIEA in DMF (v/v) were added and the mixture was vortexed at 20° C. for 16 hours and subsequently concentrated under high vacuum. The residue was partitioned between $CH_2Cl_2$ and $H_2O/CH_3CN$ (90/10; v/v). The $CH_2Cl_2$ phase was evaporated to yield the fully protected cyclic peptide.

Deprotection of the Cyclic Peptide

The cyclic peptide obtained was dissolved in 1 ml of the cleavage mixture containing 95% trifluoroacetic acid (TFA), 2.5% water and 2.5% triisopropylsilane TIS). The mixture was left to stand at 20° C. for 2.5 hours and then concentrated under vacuum. The residue was dissolved in a solution of $H_2O$/acetic acid (75/25: v/v) and the mixture extracted with diisopropylether.

The water phase was dried under vacuum and then the product purified by preparative reverse phase HPLC.

Guanidinylation of the Side Chain Amine Functions with Diprotected Triflyl-Guanidines 8 mg of the deprotected cyclic peptide and N,N-di-Boc-trifluoromethanesulfonylguanidine (270 mg, 15 eq) wered dissolved in water and dioxane (3 ml, 1:5; v/v). Triethylamine (190 µl, 15 eq) was added and the solution was stirred at room temperature for 72 h. The solution was concentrated under vacuum to remove dioxane. Water (1 ml) and $CH_2Cl_2$ (1 ml) was added. The extracted $CH_2Cl_2$ phase was econcentrated. The residue was redissolved in a mixture of TFA and $CH_2Cl_2$ (1:1, 2 ml) for 1 h at room temperature. The solution was then triturated with diethyl ether, the organic layer was removed and the residue dried in vacuo.

Purification of the Cyclic Peptide

After lyophilisation the products were obtained as white powders and analysed by ESI-MS. The analytical data comprising HPLC retention times and ESI-MS are shown in table 1. Analytical HPLC retention times (RT, in minutes) were determined using a VYDAC 218TP104 (length 25 cm) column with gradient A (50% $CH_3CN$+0.1% TFA and 50% $H_2O$+0.1% TFA to 100% $CH_3CN$+0.1% TFA and 0% $H_2O$+0.1% TFA in 25 minutes) or gradient B using solvents A ($H_2O$+0.02% TFA) and B ($CH_3CN$) 0 min: 92% A, 8% B; 8 min: 62% A 38% B; 9-12 min: 0% A, 100% B.

Purification was done using preparative reverse phase HPLC with gradient C: 10% $CH_3CN$+0.1% TFA and 90% $H_2O$+0.1% TFA to 60% $CH_3CN$+0.1% TFA and 40% $H_2O$+ 0.1% TFA in 20 minutes.

Examples 1 and 3-6 are shown in table 1. The peptides were synthesized starting with the amino acid at position P6 which was grafted to the resin. Starting resins were (EA)G-O-chlorotritylresin; (BA)G-O-chlorotritylresin; and (PrA)G-O-chlorotritylresin, which were prepared as described above. The linear peptides were synthesized on solid support according to the above procedure in the following sequence: P7-P8-P9-P10-P11-P12-$^D$Pro-Pro-P1-P2-P3-P4-P5-P6-resin, cleaved, cyclized, deprotected and purified as indicated. HPLC-retention times (minutes) were determined using gradient A.

Example 2 is also shown in table 1. The peptide was synthesized starting with a precursor of the amino acid at position P6 which was grafted to the resin. Starting resin was (EA)G-O chlorotritylresin, which was prepared as described above. The linear peptide was synthesized on solid support according to the above procedure in the following sequence: P7-P8-P9-P10-P11-P12-$^D$Pro-Pro-P1-P2-P3-P4-P5-precursor of P6-resin, Lys being introduced at positions P9, P4 and P5.

$CH_2Cl_2$ (2.5 ml) and allowed to swell at room temperature under constant stirring for 30 min. The resin was treated with 0.415 mMol (1 eq) of the first suitably protected amino acid residue (see below) and 284 μl (4 eq) of diisopropylethylamine (DIEA) in $CH_2Cl_2$ (2.5 ml), the mixture was shaken at 25° C. for 4 hours. The resin colour changed to purple and the solution remained yellowish. The resin was shaken ($CH_2Cl_2$/MeOH/DIEA: 17/2/1), 30 ml for 30 min; then washed in the following order with $CH_2Cl_2$ (1×), DMF (1×), $CH_2Cl_2$ (1×), MeOH (1×), $CH_2Cl_2$ (1×), MeOH (1×), $CH_2Cl_2$ (2×), $Et_2O$ (2×) and dried under vacuum for 6 hours. Loading was typically 0.6-0.7 mMol/g.

The following preloaded resin was prepared: Fmoc-ProO-chlorotritylresin. The peptides were synthesized starting with the amino acid Pro which was grafted to the resin. Starting resins was Fmoc-ProO-chlorotritylresin, which was prepared as described above. The linear peptides were synthesized on solid support according to the above procedure in the following sequence: Resin-Pro-$^D$Pro-P12-P11-P10-P9-P8-P7-P6-P5-P4-P3-P2-P1, cleaved, cyclized, deprotected and purified as indicated. HPLC-retension times (minutes) were determined using the gradient B as described above. The incorporation of (PeA)G in the relevant positions of examples 7-12 was accomplished using bromo acetic acid and Boc-NH—$CH_2$—$CH_2$—$CH_2$—$CH_2$—$CH_2$—$NH_2$.

TABLE 1

Examples

| Example | Sequ.ID | P1 | P2 | P3 | P4 | P5 | P6 | P7 | P8 | P9 | P10 | P11 | P12 | Template | RT(') | %$^a$ | [MS] |
|---|---|---|---|---|---|---|---|---|---|---|---|---|---|---|---|---|---|
| 1 | SEQ ID NO:1 | Leu | Arg | Leu | Lys | Lys | (EA)G | Arg | Trp | Lys | Tyr | Arg | Val | $^D$Pro$^L$Pro | 31.4 | 68 | 1823.9 |
| 2 | SEQ ID NO:2 | Leu | Arg | Leu | hArg | hArg | (EGU)G | Arg | Trp | hAig | Tyr | Arg | Val | $^D$Pro$^L$Pro | 10.8 | 40 | 498.6* |
| 3 | SEQ ID NO:3 | Leu | Arg | Leu | Lys | Lys | (PrA)G | Arg | Trp | Lys | Tyr | Arg | Val | $^D$Pro$^L$Pro | 10.0 | 51 | 933.2** |
| 4 | SEQ ID NO:4 | Leu | Arg | Leu | Lys | Lys | (BA)G | Arg | Bip | Lys | Tyr | Arg | Val | $^D$Pro$^L$Pro | 10.5 | 63 | 1889.0 |
| 5 | SEQ ID NO:5 | Leu | Arg | Leu | (BA)G | Lys | (BA)G | Arg | Bip | Lys | Tyr | Arg | Val | $^D$Pro$^L$Pro | 11.8 | 54 | 1890.0 |
| 6 | SEQ ID NO:6 | Leu | Arg | Leu | Lys | Lys | (PrA)G | Arg | Bip | Lys | Tyr | Arg | Val | $^D$Pro$^L$Pro | 10.6 | 55 | 1902.8 |
| 7 | SeQ ID NO:7 | Arg | Trp | Leu | Lys | Lys | Arg | (PeA)G | Trp | Lys | Tyr | Tyr | Val | $^D$Pro$^L$Pro | 5.67 | 100 | 959.3** |
| 8 | SEQ ID NO:8 | Arg | Trp | Leu | Gln | (PeA)G | Arg | Arg | Trp | Lys | Tyr | Tyr | Arg | $^D$Pro$^L$Pro | 5.28/6.05 | 100 | 1015.2** |
| 9 | SEQ ID NO:9 | Arg | Trp | Leu | Lys | (PeA)G | Arg | Arg | Trp | Lys | Tyr | Tyr | Val | $^D$Pro$^L$Pro | 5.78 | 100 | 986.9** |
| 10 | SEQ ID NO:10 | Thr | Trp | Leu | Lys | (PeA)G | Arg | Arg | Trp | Lys | Tyr | Tyr | Arg | $^D$Pro$^L$Pro | 5.2 | 80 | 986.9** |
| 11 | SEQ ID NO:11 | Arg | Trp | Leu | Gln | Lys | Arg | (PeA)G | Trp | Lys | Tyr | Tyr | Arg | $^D$Pro$^L$Pro | 5.25 | 100 | 1001.3** |
| 12 | SEQ ID NO:12 | Thr | Trp | Leu | Lys | (PeA)G | Arg | Arg | Trp | Lys | Tyr | Tyr | Arg | $^D$Pro$^L$Pro | 5.27/5.93 | 70 | 987.7** |

$^a$%-purity of compounds after prep. HPLC
*M/z + 4H, z = 4
**M/z, z = 2

The protected peptide was then cleaved, cyclized, deprotected, guanidinylated and purified as indicated, the guanidinylation transforming (EA)G into (EGU)G and Lys into hArg.

HPLC-retention times (minutes) were determined using gradient A.

Examples 7-12 are shown in table 1, too.

0.5 g of 2-chlorotritylchloride resin (Barlos et al. *Tetrahedron Lett.* 1989, 30, 3943-3946) (0.83 mMol/g, 0.415 mmol) was filled into a dried flask. The resin was suspended in 2. Biological Methods 2.1. Preparation of the Peptides.

Lyophilized peptides were weighed on a Microbalance (Mettler MT5) and dissolved in sterile water containing 0.01% acetic acid.

2.2. Antimicrobial Activity of the Peptides.

The antimicrobial activities of the peptides were determined by the standard NCCLS broth microdilution method (see ref 1, below) examined in sterile 96-wells plates (Nunclon polystyrene microtiter plates) in a total volume of 100 μl. Innocula of the microorganisms were prepared with 0.5 Mcfarland standard and then diluted into Mueller-Hinton (MH) broth to give appr. $10^6$ colony forming units (CFU)/ml for bacteria Aliquots (50 μl) of the innocula were added to 50 μl of MH broth containing the peptide in serial twofold dilutions. The microorganisms used were Escherichia coli (ATCC 25922), Pseudomonas aeruginosa (P. aeruginosa) (ATCC 27853), Pseudomonas putida (ATCC 27853), Staphylococcus aureus (ATCC 29213 and ATCC 25923). Antimicrobial activities of the peptides were expressed as the minimal inhibitory concentration (MIC) in μg/ml at which no visible growth was observed after 18-20 hours of incubation of the microtiter plates at 37° C.

2.3. Hemolysis

The peptides were tested for their hemolytic activity against human red blood cells (hRBC). Fresh hRBC were washed three times with phosphate buffered saline (PBS) by centrifugation for 10 min at 2000×g. Peptides at a concentration of 100 μg/ml were incubated with 20% v/v hRBC for 1 hour at 37° C. The final erythrocyte concentration was appr. $0.9\times10^9$/ml. A value of 0% resp. 100% cell lysis was determined by incubation of the hRBC in the presence of PBS alone and resp. 0.1% Triton X-100 in $H_2O$. The samples were centrifuged and the supernatant was 20 fold diluted in PBS buffer and the optical density (OD) of the sample at 540 nM was measured. The 100% lysis value ($OD_{540}H_2O$) gave an OD of approximately 1.6-2.0. Percent hemolysis was calculated as follows: ($OD_{540}$ peptide/$OD_{540}H_2O$)×100%.

2.4. Results

The results of the experiments described above are indicated in Table 2, herein below.

REFERENCES

1. National Committee for Clinical Laboratory Standards. 1993. Methods for dilution antimicrobial susceptibility tests for bacteria that grow aerobically, 3rd ed. Approved standard M7-A3. National Committee for Clinical laboratory standards, Villanova, Pa.
2. Mossman T. J Immunol Meth 1983, 65, 55-63
3. Berridge M V, Tan A S. Archives of Biochemistry & Biophysics 1993, 303, 474-482

TABLE 2

Minimal inhibitory concentrations (MIC in μg/ml) and percentage hemolyses at a concentration of 100 μg/ml of peptide

| Ex. | Escherichia coli ATCC 25922 | Pseudomonas putida ATCC 27853 | Staphylococcus aureus ATCC 29213 | Staphylococcus aureus ATCC 25923 | P. Aeruginosa ATCC27853 | Hemolyses hRBC |
|---|---|---|---|---|---|---|
| 1 | 6.2 | 6.2 | 12.5 | 12.5 | n.d. | 1.7 |
| 2 | 12.5 | 6.2 | 12.5 | 12.5 | n.d. | 8.8 |
| 3 | 25 | 12.5 | 50 | 50 | n.d. | 1.6 |
| 4 | 12.5 | 12.5 | 12.5 | 12.5 | n.d. | 4.2 |
| 5 | 6.2 | 12.5 | 6.2 | 6.2 | n.d. | 2.1 |
| 6 | 12.5 | 6.2 | 6.2 | 6.2 | n.d. | 7.0 |
| 8 | 32 | n.d. | 128 | 128 | 8 | 1.1 |
| 9 | 32 | n.d. | 128 | 128 | 16 | 1.4 |
| 10 | 64 | n.d. | 128 | 128 | 8 | 1.0 |
| 11 | 32 | n.d. | 128 | 128 | 8 | 1.1 |
| 12 | 64 | n.d. | 128 | 128 | 8 | 2.2 | n.d.: not determined

The invention claimed is:

1. A compound of the general formula

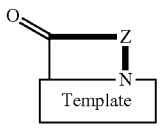

(I)

is $^D$Pro-$^L$Pro or $^L$Pro-$^D$Pro and Z is a chain of 12 amino acid residues wherein the amino acid residues in chain Z are:
P1: Leu; Thr; or Arg;
P2: Arg; or Trp;
P3: Leu;
P4: Lys; hArg [L-homo-arginine]; (BA)G [N-(4-amino-n-butyl)glycine]; or Gln;
P5: Lys; Gln; hArg; or (PeA)G [N-(5-amino-n-pentyl) glycine];
P6: Arg, Trp, hArg; (EGU)G [N-(2-guanidinoethyl)glycine]; (EA)G [N-(2-aminoethyl)glycine]; (PrA)G [N-(3-aminopropyl)glycine]; (PeA)G or (BA)G;
P7: Arg; (PeA)G; or Val;
P8: Trp; or Bip [L-(4-phenyl)phenylalanine];
P9: Lys; Arg; or hArg;
P10: Tyr;
P11: Arg; or Tyr; and
P12: Val; or Arg;
with the proviso that
the amino acid residue in P4 is (BA)G; and/or
the amino acid residue in P5 is (PeA)G; and/or
the amino acid residue in P6 is (EGU)G or (EA)G or (PrA)G or (PeA)G or (BA)G; and/or
the amino acid residue in P7 is (PeA)G or an enantiomer thereof or a pharmaceutically acceptable salt thereof.

2. The compound of formula I according to claim 1 wherein the template is $^D$Pro-$^L$Pro and the amino acid residues in position 1-12 are:
P1: Leu;
P2: Arg;
P3: Leu;
P4: Lys;
P5: Lys;
P6: (EA)G;
P7: Arg;
P8: Trp;
P9: Lys;
P10: Tyr;
P11: Arg; and
P12: Val.

3. The compound of formula Ia according to claim 1 wherein the template is $^D$Pro-$^L$Pro and the amino acid residues in position 1-12 are:
P1: Leu;
P2: Arg;
P3: Leu;
P4: hArg;
P5: hArg;
P6: (EGU)G;
P7: Arg;
P8: Trp;
P9: hArg;
P10: Tyr;
P11: Arg; and
P12: Val.

4. The compound of formula I according to claim 1 wherein the template is $^D$Pro-$^L$Pro and the amino acid residues in position 1-12 are:
P1: Leu;
P2: Arg;
P3: Leu;
P4: Lys;
P5: Lys;
P6: (PrA)G;
P7: Arg;
P8: Trp;
P9: Lys;
P10: Tyr;
P11: Arg; and
P12: Val.

5. The compound of formula I according to claim 1 wherein the template is $^D$Pro-$^L$Pro; and the amino acid residues in position 1-12 are:
P1: Leu;
P2: Arg;
P3: Leu;
P4: Lys;
P5: Lys;
P6: (BA)G;
P7: Arg;
P8: Bip;
P9: Lys;
P10: Tyr;
P11: Arg; and
P12: Val.

6. The compound of formula I according to claim 1 wherein the template is $^D$Pro-$^L$Pro and the amino acid residues in position 1-12 are:
P1: Leu;
P2: Arg;
P3: Leu;
P4: (BA)G;
P5: Lys;
P6: (BA)G;
P7: Arg;
P8: Bip;
P9: Lys;
P10: Tyr;
P11: Arg; and
P12: Val.

7. The compound of formula I according to claim 1 wherein the template is $^D$Pro-$^L$Pro and the amino acid residues in position 1-12 are:
P1: Leu;
P2: Arg;
P3: Leu;
P4: Lys;
P5: Lys;
P6: (PrA)G;
P7: Arg;
P8: Bip;
P9: Lys;
P10: Tyr;
P11: Arg; and
P12: Val.

8. The compound of formula I according to claim 1 wherein the template is $^D$Pro-$^L$Pro and the amino acid residues in position 1-12 are:
P1: Arg;
P2: Trp;
P3: Leu;
P4: Lys;
P5: Lys;
P6: Arg;
P7: (PeA)G;
P8: Trp;
P9: Lys;
P10: Tyr;
P11: Tyr; and
P12: Val.

9. The compound of formula I according to claim 1 wherein the template is $^D$Pro-$^L$Pro and the amino acid residues in position 1-12 are:
P1: Arg;
P2: Trp;
P3: Leu;
P4: Gln;
P5: (PeA)G;
P6: Arg;
P7: Arg;
P8: Trp;
P9: Lys;
P10: Tyr;
P11: Tyr; and
P12: Arg.

10. The compound of formula I according to claim 1 wherein the template is $^D$Pro-$^L$Pro and the amino acid residues in position 1-12 are:
P1: Arg;
P2: Trp;
P3: Leu;
P4: Lys;
P5: (PeA)G;
P6: Arg;
P7: Arg;
P8: Trp;
P9: Lys;
P10: Tyr;
P11: Tyr; and
P12: Val.

11. The compound of formula I according to claim 1 wherein the template is $^D$Pro-$^L$Pro and the amino acid residues in position 1-12 are:
P1: Thr;
P2: Trp;
P3: Leu;
P4: Lys;
P5: (PeA)G;
P6: Arg;
P7: Arg;
P8: Trp;
P9: Lys;
P10: Tyr;
P11: Tyr; and
P12: Arg.

12. The compound of formula I according to claim 1 wherein the template is $^D$Pro-$^L$Pro and the amino acid residues in position 1-12 are:
P1: Arg;
P2: Trp;
P3: Leu;
P4: Gln;
P5: Lys;
P6: Arg;
P7: (PeA)G;
P8: Trp;

P9: Lys;
P10: Tyr;
P11: Tyr; and
P12: Arg.

13. The compound of formula I according to claim 1 wherein the template is $^D$Pro-$^L$Pro and the amino acid residues in position 1-12 are:
P1: Thr;
P2: Trp;
P3: Leu;
P4: Lys;
P5: (PeA)G;
P6: Arg;
P7: Arg;
P8: Trp;
P9: Lys;
P10: Tyr;
P11: Tyr; and
P12: Arg.

14. A pharmaceutical composition containing a compound according to claim 1 and a pharmaceutically inert carrier.

15. The composition according to claim 14 in a form suitable for oral, topical, transdermal, injection, buccal, transmucosal, pulmonary or inhalation administration.

16. The composition according to claim 14 in form of tablets, dragees, capsules, solutions, liquids, gels, plaster, creams, ointments, syrup, slurries, suspensions, spray, nebuliser or suppositories.

17. A method for treating or reducing the risk of bacterial infections comprising administering to a patient in need thereof an effective amount of a compound according to claim 1.

18. A method for disinfecting or preserving foodstuffs, cosmetics, medicaments and other nutrient-containing materials which comprises adding to such foodstuffs, cosmetics, medicaments and other nutrient-containing materials an effective amount of a compound according to claim 1.

19. A process for the manufacture of a compound according to claim 1 which process comprises
(a) coupling an appropriately functionalized solid support with an appropriately N-protected derivative of that amino acid which in the desired end-product is in position 5, 6 or 7, any functional group which may be present in said N-protected amino acid derivative being likewise appropriately protected;
(b) removing the N-protecting group from the product thus obtained;
(c) coupling the product thus obtained with an appropriately N-protected derivative of that amino acid which in the desired end-product is one position nearer the N-terminal amino acid residue, any functional group which may be present in said N-protected amino acid derivative being likewise appropriately protected;
(d) removing the N-protecting group from the product thus obtained;
(e) repeating steps (c) and (d) until the N-terminal amino acid residue has been introduced;
(f) coupling the product thus obtained with a compound of the general formula

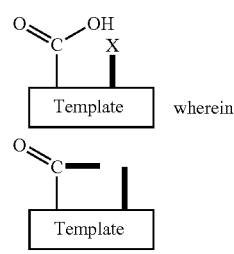

wherein is as defined above and X is an N-protecting group or, alternatively
(fa) coupling the product obtained in step (e) with an appropriately N-protected derivative of an amino acid of the general formula

HOOC—B—H     III or

HOOC-A-H     IV wherein B and A are as defined above, any functional group which may be present in said N-protected amino acid derivative being likewise appropriately protected;
(fb) removing the N-protecting group from the product thus obtained; and
(fc) coupling the product thus obtained with an appropriately N-protected derivative of an amino acid of the above general formula IV and, respectively, III, any functional group which may be present in said N-protected amino acid derivative being likewise appropriately protected;
(g) removing the N-protecting group from the product obtained in step (f) or (fc);
(h) coupling the product thus obtained with an appropriately N-protected derivative of that amino acid which in the desired end-product is in position 12, any functional group which may be present in said N-protected amino acid derivative being likewise appropriately protected;
(i) removing the N-protecting group from the product thus obtained;
(j) coupling the product thus obtained with an appropriately N-protected derivative of that amino acid which in the desired end-product is one position farther away from position 12, any functional group which may be present in said N-protected amino acid derivative being likewise appropriately protected;
(k) removing the N-protecting group from the product thus obtained;
(l) repeating steps (j) and (k) until all amino acid residues have been introduced;
(m) if desired, selectively deprotecting one or several protected functional group(s) present in the molecule and appropriately substituting the reactive group(s) thus liberated;
(o) detaching the product thus obtained from the solid support;
(p) cyclizing the product cleaved from the solid support;
(q) if desired, forming one or two interstrand linkage(s) between side-chains of appropriate amino acid residues at opposite positions of the β-strand region;

(r) removing any protecting groups present on functional groups of any members of the chain of amino acid residues and, if desired, any protecting group(s) which may in addition be present in the molecule;

(s) if desired guanidinylating any side-chain amino group present in the chain of amino acid residues; and (t) if desired, converting the product thus obtained into a pharmaceutically acceptable salt or converting a pharmaceutically acceptable, or unacceptable, salt thus obtained into the corresponding free compound of formula I or into a different, pharmaceutically acceptable, salt.

20. A process for the manufacture of a compound according to claim 1 which process comprises (a') coupling an appropriately functionalized solid support with a compound of the general formula

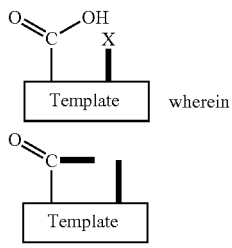

wherein is as defined above and X is an N-protecting group or, alternatively (a'a) coupling said appropriately functionalized solid support with an appropriately N-protected derivative of an amino acid of the general formula

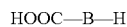 HOOC—B—H    III or

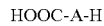 HOOC-A-H    IV wherein B and A are as defined above, any functional group which may be present in said N-protected amino acid derivative being likewise appropriately protected;

(a'b) removing the N-protecting group from the product thus obtained; and (a'c) coupling the product thus obtained with an appropriately N-protected derivative of an amino acid of the above general formula IV and, respectively, III, any functional group which may be present in said N-protected amino acid derivative being likewise appropriately protected;

(b') removing the N-protecting group from the product obtained in step (a') or (a'c);

(c') coupling the product thus obtained with an appropriately N-protected derivative of that amino acid which in the desired end-product is one position nearer the N-terminal amino acid residue, any functional group which may be present in said N-protected amino acid derivative being likewise appropriately protected;

(d') removing the N-protecting group from the product thus obtained;

(e') coupling the product thus obtained with an appropriately N-protected derivative of that amino acid which in the desired end-product is one position farther away from position 12, any functional group which may be present in said N-protected amino acid derivative being likewise appropriately protected;

(f') removing the N-protecting group from the product thus obtained;

(g') repeating steps (e') and (f') until all amino acid residues have been introduced;

(h') if desired, selectively deprotecting one or several protected functional group(s) present in the molecule and appropriately substituting the reactive group(s) thus liberated;

(i') detaching the product thus obtained from the solid support;

(j') cyclizing the product cleaved from the solid support;

(k') if desired forming one or two interstrand linkage(s) between side-chains of appropriate amino acid residues at opposite positions of the β-strand region;

(l') removing any protecting groups present on functional groups of any members of the chain of amino acid residues and, if desired, any protecting group(s) which may in addition be present in the molecule;

(m') if desired guanidinylating any side-chain amino group present in the chain of amino acid residues; and (n') if desired, converting the product thus obtained into a pharmaceutically acceptable salt or converting a pharmaceutically acceptable, or unacceptable, salt thus obtained into the corresponding free compound of formula I or into a different, pharmaceutically acceptable, salt.

21. A process for the manufacture of a compound according to claim 1, which process comprises (a) coupling an appropriately functionalized solid support with an appropriately N-protected derivative of that amino acid which in the desired end-product is in position 5, 6 or 7, any functional group which may be present in said N-protected amino acid derivative being likewise appropriately protected;

(b) removing the N-protecting group from the product thus obtained;

(c) coupling the product thus obtained with an appropriately N-protected derivative of that amino acid which in the desired end-product is one position nearer the N-terminal amino acid residue, any functional group which may be present in said N-protected amino acid derivative being likewise appropriately protected;

(d) removing the N-protecting group from the product thus obtained;

(e) repeating steps (c) and (d) until the N-terminal amino acid residue has been introduced;

(f) coupling the product thus obtained with a compound of the general formula

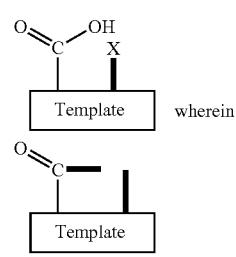

wherein is as defined above and X is an N-protecting group or, alternatively (fa) coupling the product obtained in step (e) with an appropriately N-protected derivative of an amino acid of the general formula

HOOC—B—H  III or

HOOC-A-H  IV wherein B and A are as defined above, any functional group which may be present in said N-protected amino acid derivative being likewise appropriately protected;
(fb) removing the N-protecting group from the product thus obtained; and
(fc) coupling the product thus obtained with an appropriately N-protected derivative of an amino acid of the above general formula IV and, respectively, III, any functional group which may be present in said N-protected amino acid derivative being likewise appropriately protected;
(g) removing the N-protecting group from the product obtained in step (f) or (fc);
(h) coupling the product thus obtained with an appropriately N-protected derivative of that amino acid which in the desired end-product is in position 12, any functional group which may be present in said N-protected amino acid derivative being likewise appropriately protected;
(i) removing the N-protecting group from the product thus obtained;
(j) coupling the product thus obtained with an appropriately N-protected derivative of that amino acid which in the desired end-product is one position farther away from position 12, any functional group which may be present in said N-protected amino acid derivative being likewise appropriately protected;
(k) removing the N-protecting group from the product thus obtained;
(l) repeating steps (j) and (k) until all amino acid residues have been introduced;
(m) if desired, selectively deprotecting one or several protected functional group(s) present in the molecule and appropriately substituting the reactive group(s) thus liberated;
(o) detaching the product thus obtained from the solid support;
(p) cyclizing the product cleaved from the solid support;
(q) if desired, forming one or two interstrand linkage(s) between side-chains of appropriate amino acid residues at opposite positions of the β-strand region;
(r) removing any protecting groups present on functional groups of any members of the chain of amino acid residues and, if desired, any protecting group(s) which may in addition be present in the molecule;
(s) if desired guanidinylating any side-chain amino group present in the chain of amino acid residues; and
(t) if desired, converting the product thus obtained into a pharmaceutically acceptable salt or converting a pharmaceutically acceptable, or unacceptable, salt thus obtained into the corresponding free compound of formula I or into a different, pharmaceutically acceptable salt, wherein a residue of (BA)G, (PeA)G, (EGU)G, (EA)G or (PrA)G is introduced by coupling with a leaving group-containing agent, followed by nucleophilic displacement with ammonia or guanidine.

22. A process according to claim 21 wherein said leaving group-containing agent is bromo, chloro or iodo acetic acid.

23. A process for the manufacture of a compound according to claim 1, which process comprises
(a') coupling an appropriately functionalized solid support with a compound of the general formula

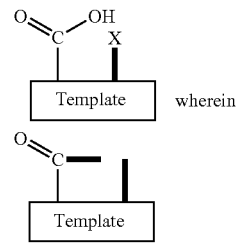

wherein is as defined above and X is an N-protecting group or, alternatively
(a'a) coupling said appropriately functionalized solid support with an appropriately N-protected derivative of an amino acid of the general formula

HOOC—B—H  III or

HOOC-A-H  IV wherein B and A are as defined above, any functional group which may be present in said N-protected amino acid derivative being likewise appropriately protected;
(a'b) removing the N-protecting group from the product thus obtained; and
(a'c) coupling the product thus obtained with an appropriately N-protected derivative of an amino acid of the above general formula IV and, respectively, III, any functional group which may be present in said N-protected amino acid derivative being likewise appropriately protected;
(b') removing the N-protecting group from the product obtained in step (a') or (a'c);
(c') coupling the product thus obtained with an appropriately N-protected derivative of that amino acid which in the desired end-product is one position nearer the N-terminal amino acid residue, any functional group which may be present in said N-protected amino acid derivative being likewise appropriately protected;
(d') removing the N-protecting group from the product thus obtained;
(e') coupling the product thus obtained with an appropriately N-protected derivative of that amino acid which in the desired end-product is one position farther away from position 12, any functional group which may be present in said N-protected amino acid derivative being likewise appropriately protected;
(f') removing the N-protecting group from the product thus obtained;
(g') repeating steps (e') and (f') until all amino acid residues have been introduced;
(h') if desired, selectively deprotecting one or several protected functional group(s) present in the molecule and appropriately substituting the reactive group(s) thus liberated;
(i') detaching the product thus obtained from the solid support;
(j') cyclizing the product cleaved from the solid support;

(k') if desired forming one or two interstrand linkage(s) between side-chains of appropriate amino acid residues at opposite positions of the β-strand region;

(l') removing any protecting groups present on functional groups of any members of the chain of amino acid residues and, if desired, any protecting group(s) which may in addition be present in the molecule;

(m') if desired guanidinylating any side-chain amino group present in the chain of amino acid residues; and (n') if desired, converting the product thus obtained into a pharmaceutically acceptable salt or converting a pharmaceutically acceptable, or unacceptable, salt thus obtained into the corresponding free compound of formula I or into a different, pharmaceutically acceptable salt, wherein a residue of (BA)G, (PeA)G, (EGU)G, (EA)G or (PrA)G is introduced by coupling with a leaving group-containing agent, followed by nucleophilic displacement with ammonia or guanidine.

24. A process according to claim 23 wherein said leaving group-containing agent is bromo, chloro or iodo acetic acid.

25. A method of treating Cystic Fibrosis comprising administering to a patient in need thereof a compound of claim 1.

* * * * *

SEQUENCE LISTING

```
<160> NUMBER OF SEQ ID NOS: 12

<210> SEQ ID NO 1
<211> LENGTH: 14
<212> TYPE: PRT
<213> ORGANISM: Artificial Sequence
<220> FEATURE:
<223> OTHER INFORMATION: Antimicrobial synthetic peptide based on
      Protegrin 1
<220> FEATURE:
<221> NAME/KEY: MISC_FEATURE
<222> LOCATION: (6)..(6)
<223> OTHER INFORMATION: Xaa in position 6 is (EA)G
<220> FEATURE:
<221> NAME/KEY: MISC_FEATURE
<222> LOCATION: (13)..(13)
<223> OTHER INFORMATION: Pro in position 13 is D-Pro

<400> SEQUENCE: 1

Leu Arg Leu Lys Lys Xaa Arg Trp Lys Tyr Arg Val Pro Pro
1               5                   10
```

```
<210> SEQ ID NO 2
<211> LENGTH: 14
<212> TYPE: PRT
<213> ORGANISM: Artificial Sequence
<220> FEATURE:
<223> OTHER INFORMATION: Antimicrobial synthetic peptide based on
      Protegrin 1
<220> FEATURE:
<221> NAME/KEY: MISC_FEATURE
<222> LOCATION: (4)..(4)
<223> OTHER INFORMATION: Xaa in position 4 is hArg
<220> FEATURE:
<221> NAME/KEY: MISC_FEATURE
<222> LOCATION: (5)..(5)
<223> OTHER INFORMATION: Xaa in position 5 is hArg
<220> FEATURE:
<221> NAME/KEY: MISC_FEATURE
<222> LOCATION: (6)..(6)
<223> OTHER INFORMATION: Xaa in position 6 is (EGU)G
<220> FEATURE:
<221> NAME/KEY: MISC_FEATURE
<222> LOCATION: (9)..(9)
<223> OTHER INFORMATION: Xaa in position 9 is hArg
<220> FEATURE:
<221> NAME/KEY: MISC_FEATURE
<222> LOCATION: (13)..(13)
<223> OTHER INFORMATION: Pro in position 13 is D-Pro

<400> SEQUENCE: 2

Leu Arg Leu Xaa Xaa Xaa Arg Trp Xaa Tyr Arg Val Pro Pro
1               5                  10

<210> SEQ ID NO 3
<211> LENGTH: 14
<212> TYPE: PRT
<213> ORGANISM: Artificial Sequence
<220> FEATURE:
<223> OTHER INFORMATION: Antimicrobial synthetic peptide based on
      Protegrin1
<220> FEATURE:
<221> NAME/KEY: MISC_FEATURE
<222> LOCATION: (6)..(6)
<223> OTHER INFORMATION: Xaa in position 6 is (PrA)G
<220> FEATURE:
<221> NAME/KEY: MISC_FEATURE
<222> LOCATION: (13)..(13)
<223> OTHER INFORMATION: Pro in position 13 is D-Pro

<400> SEQUENCE: 3

Leu Arg Leu Lys Lys Xaa Arg Trp Lys Tyr Arg Val Pro Pro
1               5                  10

<210> SEQ ID NO 4
<211> LENGTH: 14
<212> TYPE: PRT
<213> ORGANISM: Artificial Sequence
<220> FEATURE:
<223> OTHER INFORMATION: Antimicrobial Synthetic peptide based on
      Protegrin 1
<220> FEATURE:
<221> NAME/KEY: MISC_FEATURE
<222> LOCATION: (6)..(6)
<223> OTHER INFORMATION: Xaa in position 6 is (BA)G
<220> FEATURE:
<221> NAME/KEY: MISC_FEATURE
<222> LOCATION: (8)..(8)
<223> OTHER INFORMATION: Xaa in position 8 is Bip
<220> FEATURE:
<221> NAME/KEY: MISC_FEATURE
<222> LOCATION: (13)..(13)
<223> OTHER INFORMATION: Pro in position 13 is D-Pro

<400> SEQUENCE: 4
```

```
Leu Arg Leu Lys Lys Xaa Arg Xaa Lys Tyr Arg Val Pro Pro
1               5                   10
```

<210> SEQ ID NO 5
<211> LENGTH: 14
<212> TYPE: PRT
<213> ORGANISM: Artificial Sequence
<220> FEATURE:
<223> OTHER INFORMATION: Antimicrobial synthetic peptide based on
      Protegrin 1
<220> FEATURE:
<221> NAME/KEY: MISC_FEATURE
<222> LOCATION: (4)..(4)
<223> OTHER INFORMATION: Xaa in position 4 is (BA)G
<220> FEATURE:
<221> NAME/KEY: MISC_FEATURE
<222> LOCATION: (6)..(6)
<223> OTHER INFORMATION: Xaa in position 6 is (BA)G
<220> FEATURE:
<221> NAME/KEY: MISC_FEATURE
<222> LOCATION: (8)..(8)
<223> OTHER INFORMATION: Xaa in position 8 is Bip
<220> FEATURE:
<221> NAME/KEY: MISC_FEATURE
<222> LOCATION: (13)..(13)
<223> OTHER INFORMATION: Pro in position 13 is D-Pro

<400> SEQUENCE: 5

```
Leu Arg Leu Xaa Lys Xaa Arg Xaa Lys Tyr Arg Val Pro Pro
1               5                   10
```

<210> SEQ ID NO 6
<211> LENGTH: 14
<212> TYPE: PRT
<213> ORGANISM: Artificial Sequence
<220> FEATURE:
<223> OTHER INFORMATION: Antimicrobial synthetic peptide based on
      Protegrin 1
<220> FEATURE:
<221> NAME/KEY: MISC_FEATURE
<222> LOCATION: (6)..(6)
<223> OTHER INFORMATION: Xaa in position 6 is (PrA)G
<220> FEATURE:
<221> NAME/KEY: MISC_FEATURE
<222> LOCATION: (8)..(8)
<223> OTHER INFORMATION: Xaa in position 8 is Bip
<220> FEATURE:
<221> NAME/KEY: MISC_FEATURE
<222> LOCATION: (13)..(13)
<223> OTHER INFORMATION: Pro in pistion 13 is D-Pro

<400> SEQUENCE: 6

```
Leu Arg Leu Lys Lys Xaa Arg Xaa Lys Tyr Arg Val Pro Pro
1               5                   10
```

<210> SEQ ID NO 7
<211> LENGTH: 14
<212> TYPE: PRT
<213> ORGANISM: Artificial Sequence
<220> FEATURE:
<223> OTHER INFORMATION: Antimicrobial synthetic peptide based on
      Protegrin 1
<220> FEATURE:
<221> NAME/KEY: MISC_FEATURE
<222> LOCATION: (7)..(7)
<223> OTHER INFORMATION: Xaa in position 7 is (PeA)G
<220> FEATURE:
<221> NAME/KEY: MISC_FEATURE
<222> LOCATION: (13)..(13)
<223> OTHER INFORMATION: Pro in position 13 is D-Pro

<400> SEQUENCE: 7

```
Arg Trp Leu Lys Lys Arg Xaa Trp Lys Tyr Tyr Val Pro Pro
```

<210> SEQ ID NO 8
<211> LENGTH: 14
<212> TYPE: PRT
<213> ORGANISM: Artificial Sequence
<220> FEATURE:
<223> OTHER INFORMATION: Antimicrobial synthetic peptide based on
      Protegrin 1
<220> FEATURE:
<221> NAME/KEY: MISC_FEATURE
<222> LOCATION: (5)..(5)
<223> OTHER INFORMATION: Xaa in position 5 is (PeA)G
<220> FEATURE:
<221> NAME/KEY: MISC_FEATURE
<222> LOCATION: (13)..(13)
<223> OTHER INFORMATION: Pro in position 13 is D-Pro

<400> SEQUENCE: 8

Arg Trp Leu Gln Xaa Arg Arg Trp Lys Tyr Tyr Arg Pro Pro
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Antimicrobial synthetic peptide based on
      Protegrin 1
<220> FEATURE:
<221> NAME/KEY: MISC_FEATURE
<222> LOCATION: (5)..(5)
<223> OTHER INFORMATION: Xaa in position 5 is (PeA)G
<220> FEATURE:
<221> NAME/KEY: MISC_FEATURE
<222> LOCATION: (13)..(13)
<223> OTHER INFORMATION: Pro in position 13 is D-Pro

<400> SEQUENCE: 9

Arg Trp Leu Lys Xaa Arg Arg Trp Lys Tyr Tyr Val Pro Pro
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Antimicrobial synthetic peptide based on
      Protegrin 1
<220> FEATURE:
<221> NAME/KEY: MISC_FEATURE
<222> LOCATION: (5)..(5)
<223> OTHER INFORMATION: Xaa in position 5 is (PeA)G
<220> FEATURE:
<221> NAME/KEY: MISC_FEATURE
<222> LOCATION: (13)..(13)
<223> OTHER INFORMATION: Pro in position 13 is D-Pro

<400> SEQUENCE: 10

Thr Trp Leu Lys Xaa Arg Arg Trp Lys Tyr Tyr Arg Pro Pro
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Antimicrobial synthetic peptide based on
      Protegrin 1
<220> FEATURE:
<221> NAME/KEY: MISC_FEATURE
<222> LOCATION: (7)..(7)

```
<223> OTHER INFORMATION: Xaa in position 7 is (PeA)G
<220> FEATURE:
<221> NAME/KEY: MISC_FEATURE
<222> LOCATION: (13)..(13)
<223> OTHER INFORMATION: Pro in position 13 is D-Pro

<400> SEQUENCE: 11

Arg Trp Leu Gln Lys Arg Xaa Trp Lys Tyr Tyr Arg Pro Pro
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Antimicrobial synthetic peptide based on
      Protegrin 1
<220> FEATURE:
<221> NAME/KEY: MISC_FEATURE
<222> LOCATION: (5)..(5)
<223> OTHER INFORMATION: Xaa in position 5 is (PeA)G
<220> FEATURE:
<221> NAME/KEY: MISC_FEATURE
<222> LOCATION: (13)..(13)
<223> OTHER INFORMATION: Pro in position 13 is D-Pro

<400> SEQUENCE: 12

Thr Trp Leu Lys Xaa Arg Arg Trp Lys Tyr Tyr Arg Pro Pro
1               5                   10
```